United States Patent
Patil

(10) Patent No.: US 10,447,972 B2
(45) Date of Patent: Oct. 15, 2019

(54) INFANT MONITORING SYSTEM

(71) Applicant: Chigru Innovations (OPC) Private Limited, Bangalore (IN)

(72) Inventor: Radhika Patil, Bangalore (IN)

(73) Assignee: Chigru Innovations (OPC) Private Limited, Bengaluru (IN)

( * ) Notice: Subject to any disclaimer, the term of this patent is extended or adjusted under 35 U.S.C. 154(b) by 183 days.

(21) Appl. No.: 15/469,586

(22) Filed: Mar. 27, 2017

(65) Prior Publication Data
US 2018/0035082 A1 Feb. 1, 2018

(30) Foreign Application Priority Data
Jul. 28, 2016 (IN) .............................. 201641025835

(51) Int. Cl.
*A61B 5/024* (2006.01)
*H04N 7/18* (2006.01)
(Continued)

(52) U.S. Cl.
CPC ............... *H04N 7/183* (2013.01); *A47D 9/02* (2013.01); *A47D 15/00* (2013.01); *A61B 5/002* (2013.01);
(Continued)

(58) Field of Classification Search
CPC ............ G08B 21/0208; G08B 21/0202; G06K 9/00771; G06K 9/628; G06K 9/4604;
(Continued)

(56) References Cited

U.S. PATENT DOCUMENTS 6,130,956 A * 10/2000 Butterworth ......... G01N 15/147
382/100
7,256,818 B2 * 8/2007 Sadok .................. G08B 17/125
340/578

(Continued)

FOREIGN PATENT DOCUMENTS

CN 20237772 * 5/2013
CN 20399185 * 12/2014
(Continued)

OTHER PUBLICATIONS

Written Opinion of the International Searching Authority, Co-pending PCT International application No. PCT/IN2017/050276 (filing date: Jul. 6, 2017), dated Sep. 13, 2017, pp. 1-3.
(Continued)

*Primary Examiner* — Philip P. Dang
(74) *Attorney, Agent, or Firm* — IPHorizons PLLC; Narendra Reddy Thappeta

(57) ABSTRACT

A monitoring system includes a sensor, a processing block and an alert generator. The sensor is used to generate images of an infant. The processing block processes one or more of the images and identifies a condition with respect to the infant. Then alert generator causes generation of an alert signal if the identified condition warrants external notification. In an embodiment, the sensor is a 3D camera, and the 3D camera, the processing block and the alert generator are part of a unit placed in the vicinity of the infant. The monitoring system further includes microphones and motion sensors to enable detection of sounds and movement.

13 Claims, 13 Drawing Sheets

(51) Int. Cl.
| | | |
|---|---|---|
| G06T 7/246 | (2017.01) | |
| G06T 7/90 | (2017.01) | |
| H04N 13/204 | (2018.01) | |
| A47D 9/02 | (2006.01) | |
| A47D 15/00 | (2006.01) | |
| A61B 5/08 | (2006.01) | |
| A61B 5/00 | (2006.01) | |
| A61B 7/02 | (2006.01) | |
| A61B 7/04 | (2006.01) | |
| G06K 9/00 | (2006.01) | |
| G06K 9/20 | (2006.01) | |
| G06K 9/46 | (2006.01) | |
| G06K 9/62 | (2006.01) | |
| G06T 5/20 | (2006.01) | |
| G06T 7/00 | (2017.01) | |
| G08B 21/02 | (2006.01) | |
| G10L 21/0232 | (2013.01) | |
| H04R 3/00 | (2006.01) | |
| H04R 5/027 | (2006.01) | |
| A61B 5/11 | (2006.01) | |
| G16H 40/67 | (2018.01) | |
| G16H 40/63 | (2018.01) | |
| G10L 21/0208 | (2013.01) | |
| H04N 13/00 | (2018.01) | |
| H04N 13/20 | (2018.01) | |

(52) U.S. Cl.
CPC ........ *A61B 5/0022* (2013.01); *A61B 5/02416* (2013.01); *A61B 5/0816* (2013.01); *A61B 5/1128* (2013.01); *A61B 5/45* (2013.01); *A61B 5/7278* (2013.01); *A61B 5/746* (2013.01); *A61B 7/026* (2013.01); *A61B 7/04* (2013.01); *G06K 9/0061* (2013.01); *G06K 9/00248* (2013.01); *G06K 9/00255* (2013.01); *G06K 9/00281* (2013.01); *G06K 9/00369* (2013.01); *G06K 9/00389* (2013.01); *G06K 9/00604* (2013.01); *G06K 9/00771* (2013.01); *G06K 9/209* (2013.01); *G06K 9/4604* (2013.01); *G06K 9/628* (2013.01); *G06T 5/20* (2013.01); *G06T 7/0016* (2013.01); *G06T 7/246* (2017.01); *G06T 7/90* (2017.01); *G08B 21/0202* (2013.01); *G08B 21/0208* (2013.01); *G10L 21/0232* (2013.01); *G16H 40/63* (2018.01); *G16H 40/67* (2018.01); *H04N 13/204* (2018.05); *H04R 3/005* (2013.01); *H04R 5/027* (2013.01); *A61B 5/6892* (2013.01); *A61B 2503/04* (2013.01); *G06K 2009/00939* (2013.01); *G06T 2207/10012* (2013.01); *G06T 2207/10024* (2013.01); *G06T 2207/30008* (2013.01); *G06T 2207/30041* (2013.01); *G06T 2207/30088* (2013.01); *G06T 2207/30201* (2013.01); *G06T 2207/30232* (2013.01); *G10L 21/0208* (2013.01); *H04N 13/20* (2018.05); *H04N 2013/0074* (2013.01); *H04R 2430/20* (2013.01); *Y02A 90/26* (2018.01)

(58) Field of Classification Search
CPC .. G06K 9/209; G06K 9/0061; G06K 9/00604; G06K 9/00369; G06K 9/00281; G06K 9/00255; G06K 9/00389; G06K 9/00248; G06F 19/00; G10L 21/0208; G10L 21/0232; G06T 7/0016; G06T 5/20; G06T 2207/30088; G06T 7/246; G06T 7/90; G06T 2207/10024; G06T 2207/30008; G06T 2207/30041; G06T 2207/10012; G06T 2207/30201; G06T 2207/30232; G16H 40/67; A61B 5/45; A61B 7/04; A61B 7/026; A61B 5/1128; A61B 5/0022; A61B 5/002; A61B 5/746; A61B 5/7278; A61B 2503/04; A61B 5/6892; A61B 5/02416; A61B 5/0816; A47D 9/02; A47D 15/00; H04N 7/183; H04N 13/204; H04R 5/027; H04R 3/005; H04R 2430/20

See application file for complete search history.

(56) References Cited

U.S. PATENT DOCUMENTS

| | | | | |
|---|---|---|---|---|
| 7,280,696 | B2* | 10/2007 | Zakrzewski | G06K 9/00771 382/218 |
| 7,291,118 | B2* | 11/2007 | McFarland | A61B 5/103 600/587 |
| 7,366,645 | B2* | 4/2008 | Ben-Arie | G06F 3/011 703/11 |
| 7,505,604 | B2* | 3/2009 | Zakrzewski | B64D 45/0015 382/100 |
| 7,729,510 | B2* | 6/2010 | Zakrzewski | B64D 45/0015 340/630 |
| 8,494,227 | B2* | 7/2013 | Prokoski | A61B 5/0064 382/115 |
| 8,667,519 | B2* | 3/2014 | Small | H04N 21/4223 725/10 |
| 9,087,242 | B2* | 7/2015 | Sukthankar | G06K 9/00718 |
| 9,372,123 | B2* | 6/2016 | Li | G01K 1/14 |
| 9,530,080 | B2* | 12/2016 | Glazer | H04N 5/2251 |
| 2006/0071784 | A1 | 4/2006 | Frank | |
| 2007/0287394 | A1* | 12/2007 | Swan | G08B 13/19621 455/127.5 |
| 2009/0062622 | A1* | 3/2009 | Lin | A47D 9/02 600/300 |
| 2013/0314536 | A1* | 11/2013 | Frank | H04N 5/33 348/148 |
| 2014/0093133 | A1* | 4/2014 | Frank | B60R 21/01532 382/104 |
| 2014/0177706 | A1* | 6/2014 | Fernandes | H04N 19/463 375/240.03 |
| 2014/0192135 | A1 | 7/2014 | Babineau et al. | |
| 2015/0038072 | A1 | 2/2015 | Cordier et al. | |
| 2015/0109442 | A1* | 4/2015 | Derenne | G06F 16/78 348/143 |
| 2015/0182406 | A1* | 7/2015 | Falk | A61G 11/00 600/22 |
| 2015/0229341 | A1* | 8/2015 | Fung | H04B 1/10 702/191 |
| 2015/0262134 | A1* | 9/2015 | Daley | G06Q 10/20 705/305 |
| 2015/0317793 | A1* | 11/2015 | Zhang | G06T 7/20 382/130 |
| 2016/0078272 | A1* | 3/2016 | Hammoud | G06K 9/6268 382/103 |
| 2016/0199241 | A1 | 7/2016 | Rapoport | |
| 2018/0000408 | A1* | 1/2018 | Heinrich | A61B 5/0452 |

FOREIGN PATENT DOCUMENTS

| | | |
|---|---|---|
| CN | 105792733 A | 7/2016 |
| CN | 104684465 B | 7/2017 |
| EP | 2928360 A1 | 10/2015 |
| EP | 2976998 A1 | 1/2016 |
| IN | 201647018262 A | 8/2016 |
| JP | 2017500927 A | 1/2017 |
| WO | WO2010098702 A1 | 9/2010 |
| WO | 2014012070 A1 | 1/2014 |
| WO | WO2014012070 A1 | 1/2014 |

(56) References Cited

FOREIGN PATENT DOCUMENTS

WO    WO2014012070 A1    1/2014
WO    WO2015091582 A1    6/2015

OTHER PUBLICATIONS

ISR Search Report, Co-pending PCT International application No. PCT/IN2017/050276 (filing date: Jul. 6, 2017), dated Sep. 13, 2017, pp. 1-4.

Chen-Chiung Hsieh, Dung-Hua Liou, David Lee, A real time hand gesture recognition system using motion history image, Signal Processing Systems (ICSPS), 2010 2nd International Conference, Date of Conference: Jul. 5-7, 2010, pp. 1-1, IEEE, Dalian, China.

Hong Cheng, Lu Yang, Zicheng Liu, Survey on 3D Hand Gesture Recognition, IEEE Transactions on Circuits and Systems for Video Technology, Date of Publication: Aug. 18, 2015, pp. 1659-1673, vol. 26, Issue: 9, IEEE.

V. Bevilacqua M. Caprioli, M. Cortellino, M. Giannini, G. Mastronardi, V. Santarcangelo, Accuracy of 3D Face Recognition Frameworks, ISPRS TC VII Symposium—100 Years ISPRS, Vienna, Austria, Jul. 5-7, 2010, IAPRS, vol. XXXVIII.

Xia Han, Moi Hoon Yap, Ian Palmer, Face Recognition in the Presence of Expressions, Journal of Software Engineering and Applications, Published Online May 2012, pp. 1-9.

Saad Ahmed Sirohey, Masooda Begum, Iftikhar A. Sirohey, Zarina Sirohey, Human Face Segmentation and Identification (1993), date Nov. 1993, pp. 1-39.

Oya Celiktutan, Sezer Ulukaya and Bulent Sankur, A comparative study of face landmarking techniques, EURASIP Journal on Image and Video Processing 2013, Published: Mar. 7, 2013, pp. 1-27.

Maria Consuelo Ruiz, Automatic Face Landmarking in 3D, Centre for Vision, Speech and Signal Processing Faculty of Engineering and Physical Sciences University of Surrey, date Jan. 2011, pp. 1-246.

Evangelos Kalogerakis, Aaron Hertzmann, Karan Singh. Learning 3D Mesh Segmentation and Labeling, ACM Transactions on Graphics, vol. 29, No. 3, Jul. 2010, pp. 1-13.

Andrea Tagliasacchi, Hao Zhang, Daniel Cohen-Or, Curve skeleton extraction from incomplete point cloud,ACM Transactions on Graphics (TOG)—Proceedings of ACM SIGGRAPH 2009, vol. 28 Issue 3, Aug. 2009, pp. 1-9, Article No. 71 ACM New York, NY, USA.

Julien Tierny, Jean-Philippe Vandeborre, and Mohamed Daoudi, 3D Mesh Skeleton Extraction Using Topological and Geometrical Analyses, 14th Pacific Conference on Computer Graphics and Applications (Pacific Graphics 2006), Oct. 2006, pp. 1-10, Tapei, Taiwan.

Anne Verroust, Francis Lazarus, Extracting Skeletal Curves from 3D Scattered Data, Shape Modeling and Applications, 1999. Proceedings. Shape Modeling International '99. International Conference, Date of Conference: Mar. 1-4, 1999, pp. 1-8, IEEE, Aizu-Wakamatsu, Japan, Japan.

Oscar Kin-Chung Au, Chiew-Lan Tai, Hung-Kuo Chu, Daniel Cohen-Or, Tong-Yee Lee, Skeleton Extraction by Mesh Contraction, ACM Transaction on Graphics (Proceedings of SIGGRAPH 2008, vol. 27 Issue 3, Aug. 2008, Article No. 44, pp. 1-10.

Julien Tierny, Jean-Philippe Vandeborre, Mohamed Daoudi, Topology driven 3D mesh hierarchical segmentation, Shape Modeling and Applications, 2007. SMI '07. IEEE International Conference, Date of Conference: Jun. 13-15, 2007, pp. 1-3, IEEE, Lyon, France.

* cited by examiner

INFANT MONITORING SYSTEM

PRIORITY CLAIM AND RELATED APPLICATION

The instant patent application claims priority from co-pending India provisional patent application entitled, "Infant Monitoring System", Application Number: 201641025835, Filed: 28 Jul. 2016, and is incorporated in its entirety herewith, to the extent not inconsistent with the content of the instant application.

The instant patent application is related to and claims priority from, co-pending U.S. non-provisional patent application entitled, "Rocking Cradle", Ser. No. unassigned, filed on even date herewith, and is incorporated in its entirety herewith, to the extent not inconsistent with the content of the instant application.

BACKGROUND

Technical Field

Embodiments of the present disclosure relates to monitoring systems and more specifically to an infant monitoring system.

Related Art

Infant monitoring systems are well known in the art, and are generally directed to monitoring an infant. For example, such a system may be used in a cradle to enable the determination of the condition (e.g., position/posture) of an infant placed in the cradle. Such systems may additionally contain alert mechanisms to transmit alerts if/when one or more adverse conditions are determined to be present with respect to the infant placed in the cradle.

Aspects of the present disclosure are directed to providing an infant monitoring system.

BRIEF DESCRIPTION OF THE DRAWINGS

Example embodiments of the present disclosure will be described with reference to the accompanying drawings briefly described below.

In the drawings, like reference numbers generally indicate identical, functionally similar, and/or structurally similar elements. The drawing in which an element first appears is indicated by the leftmost digit(s) in the corresponding reference number.

DETAILED DESCRIPTION

A monitoring system includes a camera, a processing block and an alert generator. The camera is used to generate images of an infant. The processing block processes one or more of the images and identifies a condition with respect to the infant. Then alert generator causes generation of an alert signal if the identified condition warrants external notification. The camera, the processing block and the alert generator are part of a unit placed in the vicinity of the infant.

In an embodiment, the camera is a 3D (three dimensional) camera. The 3D camera is used to generate images as one or more 3D (three-dimensional) images of the infant located in a field-of-view (FoV) of the 3D camera. Each 3D image is characterized by coordinates for the pixels of the image, with the coordinates specifying (in addition to color information or intensity in general) spatial location of the corresponding point/area of the object (infant).

Several aspects of the invention are described below with reference to examples for illustration. It should be understood that numerous specific details, relationships, and methods are set forth to provide a full understanding of the invention. One skilled in the relevant arts, however, will readily recognize that the invention can be practiced without one or more of the specific details, or with other methods, etc. In other instances, well-known structures or operations are not shown in detail to avoid obscuring the features of the invention.

1. Example Infant Monitoring System

Figure 1:
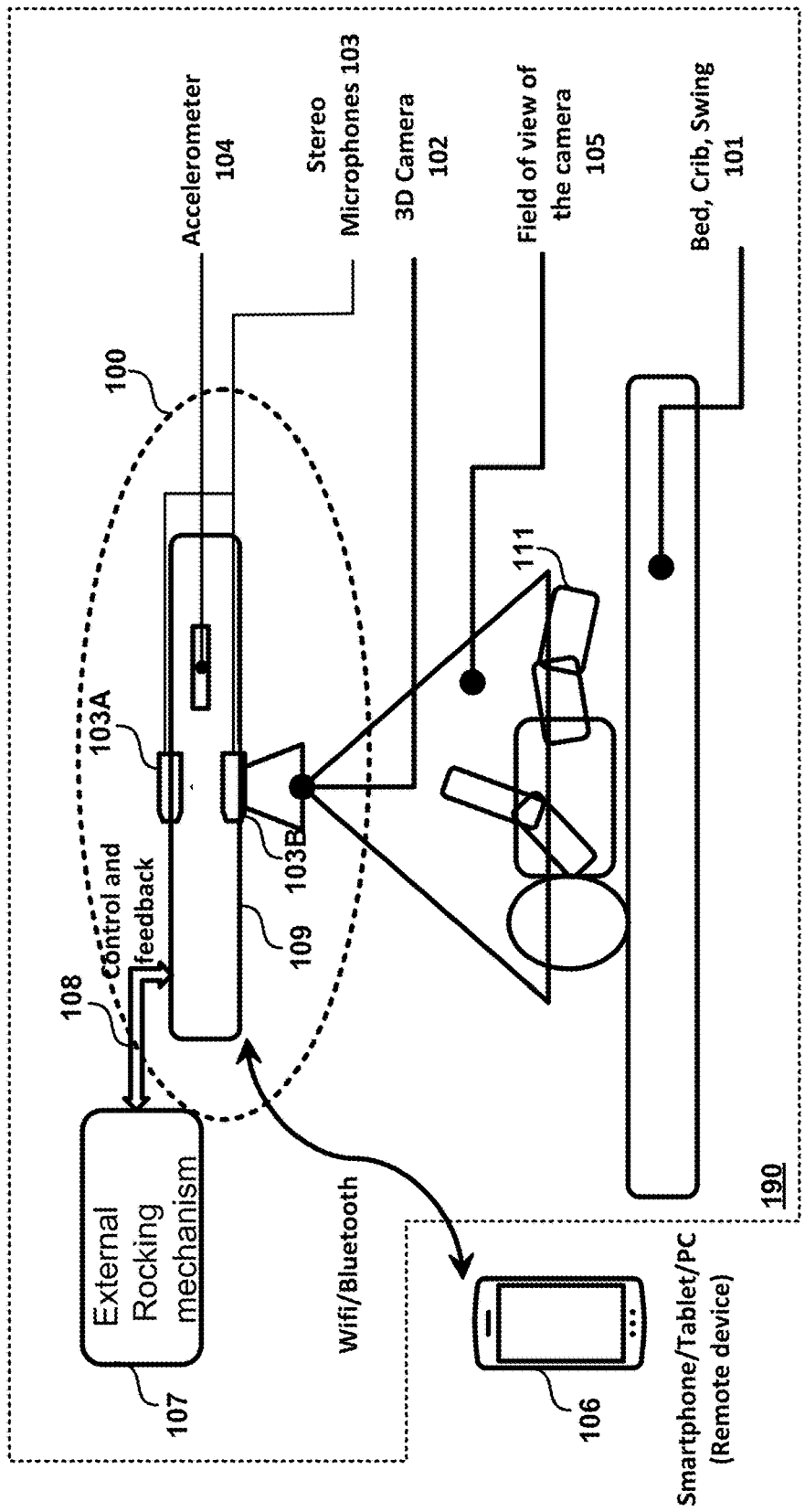
FIG. 1 is a block diagram illustrating an example monitoring system in a cradle in which several aspects of the present disclosure are implemented.

FIG. 1 is a block diagram showing an infant monitoring system according to aspects of the present disclosure. Other components and devices are also shown in FIG. 1 as described in detail below. Merely as an illustration, the infant monitoring system is described below in the context of a cradle and specifically in the context of the other components/sub-systems of FIG. 1. However, the infant monitoring system according to various aspects of the present disclosure can be deployed in other environments, in conjunction with other systems or as a stand-alone system as well. Further, while the monitoring system is described as being applied to monitoring an infant, in general the monitoring system can be applied to monitoring persons of all ages.

FIG. 1 is shown containing a cradle 190, in turn containing a bed/crib/swing 101, fixed frame 109 and external rocking mechanism 107. Crib 101, in which infant 111 may be placed, may be suspended from fixed frame 109 (the mechanism for such suspension not shown in FIG. 1), and may be designed to be able to rock or oscillate about one or more axes. External rocking mechanism 107 is used to rock/swing the crib 101 in desired modes of operation (vertical rocking and/or horizontal rocking). An example implementation of external rocking mechanism 107 is described in the co-pending U.S. non-provisional application noted above in the Related Applications section.

Fixed frame 109 may be connected to the ceiling or floor of a room, or any other stable surface by suitable means, not shown, and anchors the cradle to a stable surface. In an embodiment of the present disclosure, fixed frame 109 houses the components/sub-systems that constitute infant monitoring system 100. However, in other embodiments, the components/sub-systems of infant monitoring system 100 may be placed suitably elsewhere in the cradle. Fixed frame 109 houses accelerometer 104, a 3D (three dimensional) camera 102 and stereo microphones 103. Although not shown, infant monitoring system 100 also includes power sources (e.g., battery) and electronics/communications/processing blocks/alert generation units (as well as non-volatile memory for storing the software instructions implementing the various blocks described herein) for performing various operations described herein. Additionally, infant monitoring system 100 may contain a music system. It may thus be appreciated that 3D camera 102, the processing block and the alert generator are part of a unit (here fixed frame 109) placed in the vicinity of the infant (here infant 111 is within the field of view of 3D camera, which is a part of fixed frame 109 itself). Thus the components are all placed to be within a short distance (say utmost 10 meters, but typically more in the range of 1-2 meters), thereby providing a solution for the monitoring system individually (instead of a centralized or remote solution for monitoring many persons at different locations).

Figure 11:
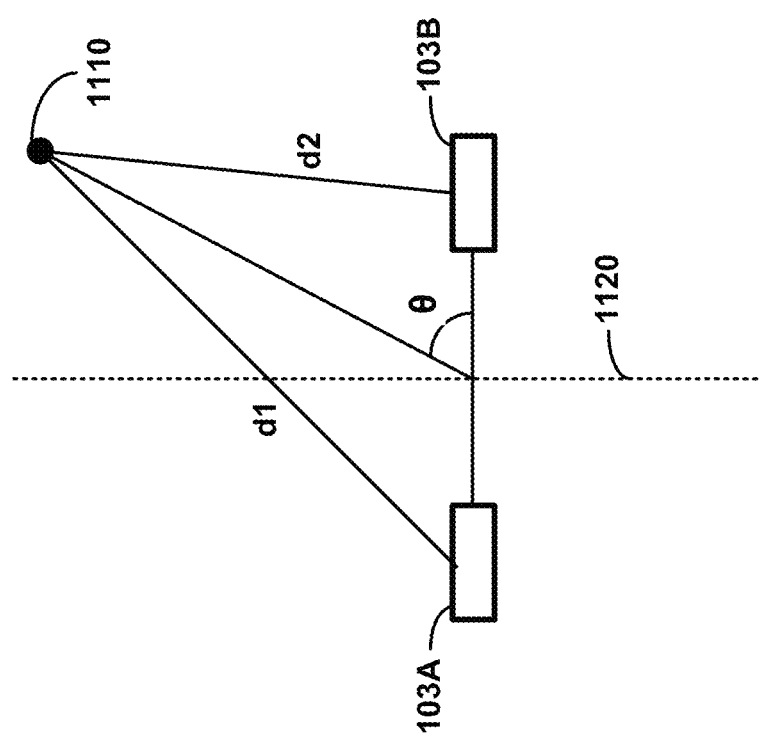
FIG. 11 is a diagram illustrating the placement of microphones in a cradle, in an embodiment of the present disclosure.

Stereo microphones 103 include at least a pair of microphones 103A and 103B. As is well known in the relevant arts, difference in time of arrival of sound at microphones 103A and 103B represents the angle of arrival of sound. As is also well known in the relevant arts, stereo microphones cannot discern between sounds originating from any point on a given cone whose axis passes through line joining the two microphones. The size of the cones gets smaller in the direction of the axis and gets biggest in the plane perpendicular to the axis. Hence it is important to have the subject near the line that joins the two microphones. With reference to FIG. 11, any point on the mid-plane 1120 is equidistant from both the microphones 103A and 103B. Therefore time-of-arrival of sound cannot be used for localizing the source of the sound (except that the source lies somewhere on the mid-plane 1120).

For other locations of the source of sound, the difference (d1−d2) between the distances of the source from 103A and 103B approximately equals sin (θ) for distances much larger than the distance between the two microphones (θ being the angle shown in FIG. 11). Hence the set of points for which difference in time-of-arrival is the same is a cone. One can observe from FIG. 11 that the cone becomes smaller as θ becomes smaller. Therefore, for minimizing the possible set of points where if the source is placed, determination of the location is difficult, subjects of interest have to ideally be placed closer to the line joining the microphones 103A and 103B. Thus, the infant (and therefore crib 111) is placed in a location that is in the line joining the microphones 103A and 103B, as can also be observed from FIG. 1. Such orientation of the microphones enables a better rejection of all other sounds in the environment.

A remote computing device 106 is paired with infant monitoring system 100 to enable alerts from (suitable transceivers such as WiFi™, Bluetooth™, etc., in) infant monitoring system 100 to be sent to a remote location so that status of infant 111 can be checked from a remote location. Examples of remote computing device 106 include a smart phone, a tablet, a personal computer (PC) or similar electronic devices.

3D camera 102 is designed to capture 3D images of objects/scene in its field of view (FoV) 105, and is implemented in an embodiment to be sensitive to light in the near-infrared spectrum. However, in other embodiments a 3D camera sensitive to other spectral regions of light can be used instead. Each 3D image contains multiple pixels/pixel locations, with each pixel specifying the intensity (color, black/white, etc.) of the point/area represented by the pixel. As noted above, each pixel is also characterized by coordinates specifying spatial location of the corresponding point/area of the object (infant) represented by the pixel. 3D camera provides a point cloud that consists of (X,Y,Z) data for each pixel and a 2D (2-dimensional) monochrome image which consists of the intensity data for each pixel. A raw 2D image is an image that consists of the intensity obtained at each pixel in the 3D camera and looks similar to an image obtained from a regular monochrome sensor/camera with a flash light or a black and white version of a color photo obtained using a regular camera and flash light.

As is well known in the relevant arts, 3D images provide depth perception, in addition to height and width. In an embodiment, 3D camera 102 may use a Time-of-Flight (ToF) sensor, well known in the relevant arts. A ToF sensor illuminates the field of view 105 of the 3D camera with one or more pulses of light (e.g., visible, near-infrared etc.). Reflection from objects in the field of view 105 that are at different distances (depths) from the ToF sensor reach the ToF sensor at different times, which is then used to determine the distances (depth component for each pixel) to the corresponding objects or portions of the scene (here infant 111 and possibly a portion of crib 101). In addition, 2D image of the scene is also obtained, disregarding the depth component.

In an alternative embodiment, 3D camera 102 is implemented using two image sensors positioned side-by-side for capturing simultaneous images of the scene/object from slightly different angles, as is also well known in the relevant arts. In each embodiment, 3D camera 102 may also include illumination sources and optical systems.

Brief details of how the 3D images, and information from the 3D images, are generated with a ToF sensor are described next.

2. Generation of 3D Image and Extraction of Skeletal Information 3D camera 102 with a ToF sensor, transmits pulses of light toward FoV 105, receives light reflected from objects (such as infant 1110 and scene in FoV 105. 3D camera 102 measures the time delay between the transmitted and the received pulses received at each pixel in 3D camera 102, and generates one or more raw distance images of the object/scene in FoV 105. 3D camera 102 (or the processing units contained within) processes the raw distance image(s) using well known techniques to obtain a depth image (3D image) consisting of x, y and z coordinates of each point in the scene in field of view 105 as well as the intensity (I) of the corresponding point. A processing block converts the 3D image to skeletal information of infant 111 using well known algorithms. Thus, for example, the top level representative skeleton is extracted using one or more of the methods described in detail in the following references:

a) Extracting Skeletal Curves from 3D Scattered Data authored by Anne Verroust and Francis Lazarus, published in Shape Modeling International '99, Aizu Wakamatsu, Mar. 1-4, 1999;

b) 3D Mesh Skeleton Extraction Using Topological and Geometrical Analyses, authored by Julien Tierny, Jean-Philippe Vandeborre and Mohamed Daoudi, published in the proceedings of the 14th Pacific Conference on Computer Graphics and Applications, Oct. 11-13, 2006, Taipei, Taiwan;

c) Curve Skeleton Extraction from Incomplete Point Cloud, authored by Andrea Tagliasacchi, Hao Zhang and Daniel Cohen-Or, published in Proceedings of SIGGRAPH '09 ACM SIGGRAPH 2009 papers, Article No. 71, New Orleans, Louisiana—Aug. 3-7, 2009.

d) Skeleton Extraction by Mesh Contraction, authored by Oscar Kin-Chung Au, Chiew-Lan Tai, Hung-Kuo Chu, Daniel Cohen-Or and Tong-Yee Lee, published in ACM Trans. Graph. 27, 3, Article 44 (August 2008).

The top level skeleton consists of line segments that represent the important parts of the human body such as the head, neck, torso, arms and legs. At this stage, the parts are not identified yet. For identification, the segmentation of the point cloud is then done using machine learning approaches, or one of the methods in the following two references:

a) Learning 3D Mesh Segmentation and Labeling, authored by Evangelos Kalogerakis, Aaron Hertzmann and Karan Singh, published in ACM transactions on Graphics 29 {3}, July 2010; and b) Topology driven 3D mesh hierarchical segmentation, authored by Julien Tierny, Jean-Philippe Vandeborre and Mohamed Daoudi, published in proceedings of the IEEE International Conference on Shape Modeling and Applications (SMI'2007), Jun. 13-15, 2007, Lyon, France.

In the machine learning approach, the obtained skeleton represented in the form of bones and joints is provided as input to a trained neural network or deep learning network to label the various bones.

After the top/first level of segmentation, the following parts are separately identified—

1. Body
   a. Head
   b. Neck
   c. Torso
      i. Chest
      ii. Belly
      iii. Hips
   d. Arms
      i. Left Arm
      ii. Right Arm
   e. Legs
      i. Left leg
      ii. Right leg The skeletal information thus obtained consists of position of bones, joints and vector representation of the bones of infant 111. Each bone may be represented by a number of points to help meet the degree of accuracy required. With respect to the palm for example, all the points where the fingers join the hands are part of the skeletal information. Each finger may be represented using three vertices, one at each joint in the finger. Additionally, details such as nose, eyes, ears etc., of infant 111 are extracted after segmenting the skeletal information and analyzing individual segments in more detail using well known algorithms, as described in sections below.

Figure 2A:
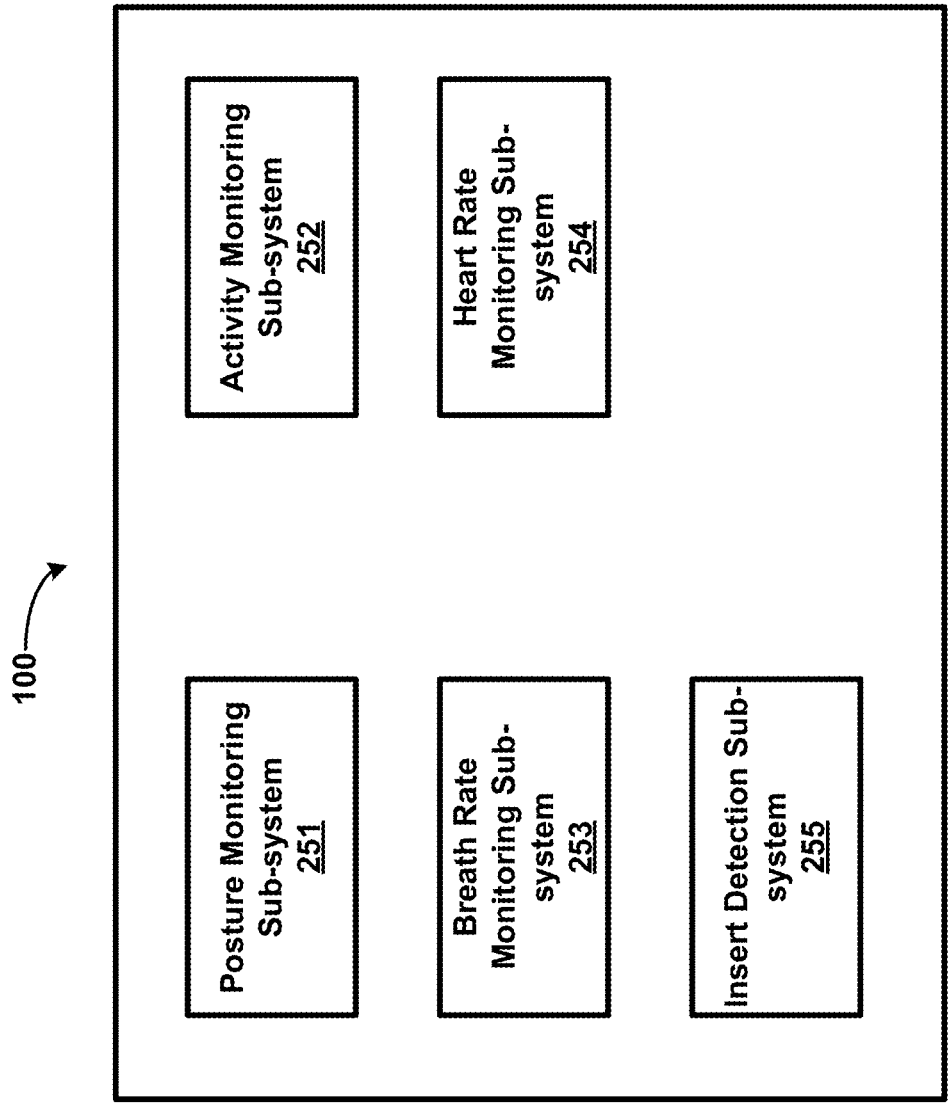
FIG. 2A is a diagram depicting the various subsystems of an infant monitoring system in an embodiment of the present disclosure.

Infant monitoring system 100 contains one or more sub-systems, each sub-system performing a corresponding sub-function independently. In an embodiment of the present disclosure, the sub-systems include posture monitoring sub-system 251, activity monitoring sub-system 252, a breath rate monitoring sub-system 253, a heart rate monitoring sub-system 254 and an insect detection sub-system 255, as depicted in FIG. 2A. FIG. 2A is a functional view of infant monitoring system 100, and each of the blocks (sub-systems) therein performs a corresponding function by execution of instructions by a processor (such as processing block 1010, described below).

Each of the sub-systems and the operations of the sub-systems are described in detail in sections below. In addition, one or more sub-blocks of the sub-systems may employ machine learning techniques. As is well known the relevant arts, machine learning approaches do not use fixed algorithms. Instead, they use artificial neural networks to train themselves over time to take the right decisions. Any machine learning algorithm consists of the following phases—

1. Initialization of algorithm through random seeding.
2. Improvisation or learning through the adjustments of weights. The algorithm is fed with vast quantities of input data and the output is compared against expected output. The weights are adjusted to move the output towards expected output. This process of feeding data and comparing against output is done several thousands or even millions of times to reduce the estimation error. This process involves expert humans who train the algorithm by providing reference outputs for a given set of inputs.
3. Testing and verification—The algorithm is tested against a fresh set of data to check the accuracy. If the accuracy is below expectations, process 2 is repeated for a larger number of times.
4. In field usage—Once the weights are trained, the algorithm is frozen for use and deployed. It is also possible in some cases that further improvisation is possible with the help of human experts who correct the outputs of the algorithm. Thus, for example, the weights of the learning machine can be updated over the air, for example via remote device 106, thereby continuing to improve the machine learning algorithm with the help of human experts.

3. Posture Monitoring Sub-System

Figure 2B:
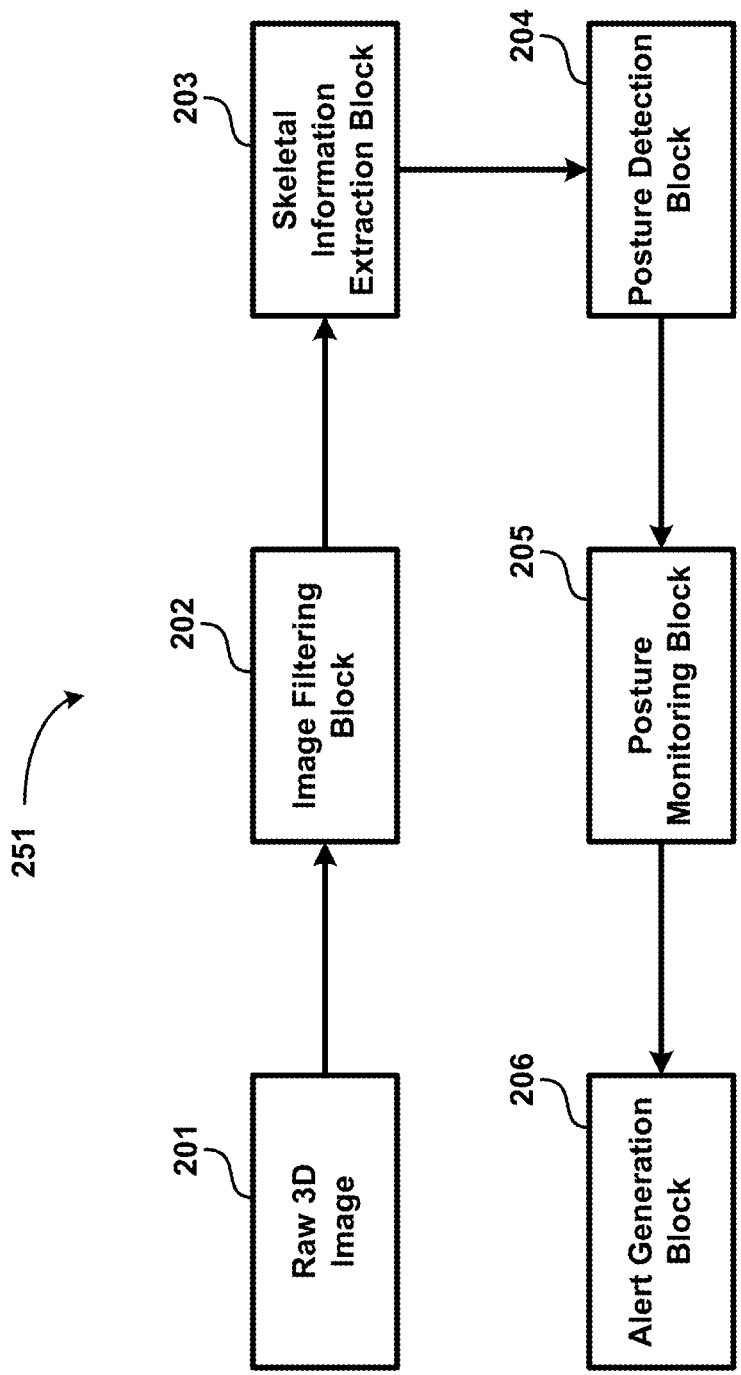
FIG. 2B is a block diagram of a posture monitoring sub-system in an embodiment of the present disclosure.

FIG. 2B is a diagram illustrating the various blocks of posture monitoring sub-system 251 in an embodiment of the present disclosure. Posture monitoring sub-system 251 is shown containing image filtering block 202, skeletal information extraction block 203, posture detection block 204, posture monitoring block 205 and alert (or alarm) generation block 206.

3D camera 102 (FIG. 1) generates one or more frames (i.e. a sequence of successive frames of) of raw 3D image 201 of a scene including the infant 111 in FoV 105. It is noted here that, depending on the nature of the next stage(s) of processing, the term raw 3D image (201) can refer to either a single frame of pixels representing a scene/object in FoV 105, or a sequences of successive images of frames at corresponding instants of time.

Image filtering block 202 filters out pixels in raw 3D image 201 that have low amplitude and high noise. Image filtering block 202 forwards the filtered image to skeletal information extraction block 203.

Skeletal information extraction block 203 extracts skeletal information from the received filtered image. The manner in which the first/top level segmentation of the body can be obtained is described above. For posture monitoring, skeletal information extraction block 203 additionally performs segmentation of the head. The obtained monochrome amplitude image and the point cloud from the 3D camera are used for further segmentation. The head segmentation is performed with the help of well-known methods presented using machine learning approaches or by using the approaches described in the following document(s)

a) PhD dissertation named Automatic Face Landmarking in 3D, by Maria Consuelo Ruiz, Centre for Vision, Speech and Signal Processing, Faculty of Engineering and Physical Sciences, University of Surrey Guildford, Surrey GU2 7XH, U.K., January 2011;

b) A comparative study of face landmarking techniques, Oya Ç eliktutan, Sezer Ulukaya and Bülent Sankur, EURASIP Journal on Image and Video Processing, 2013 2013:13, Published: 7 Mar. 2013;

c) Human face Segmentation and Identification, by Saad Ahmed Sirohey, Computer Vision Laboratory. Centre for Automation Research, University of Maryland, College Park;

d) Face Recognition in the Presence of Expressions, by Xia Han, Moi Hoon Yap, and Ian Palmer, published in Journal of Software Engineering and Applications, Vol. 5 No. 5 (2012), Article ID: 19424; and e) Accuracy of 3D Face Recognition Frameworks, by V. Bevilacqua, M. Caprioli, M. Cortellino, M. Giannini, G. Mastronardi, and V. Santarcangelo, published in: ISPRS TC VII Symposium—100 Years ISPRS, Vienna, Austria, Jul. 5-7, 2010, 0, IAPRS, Vol. XXXVIII, Part 7B.

In the machine learning approach, the 2D image of the head segment is passed through a spatial low pass filter followed by a spatial decimation filter to reduce complexity and the filtered output is provided as input to a trained neural network or deep learning network to label the various parts of the image.

After the segmentation of the head, the following parts are separately identified—

1. Head
   a. Eyes
      i. Left eye
      ii. Right eye
   b. Nose
   c. Ears
      i. Left Ear
      ii. Right Ear
   d. Nose
   e. Chin
   f. Forehead As noted above, the skeletal information includes positions of the joints and important mid-points that represent bones as well as details such as nose, eyes, ears, etc. Skeletal information block forwards the skeletal information to posture detection block 204. Skeleton may be represented hierarchically. For example, the skeleton of the whole body consists of head, torso, arms and legs. The head in turn consists of bones and cartilage that make up the nose, the chin, the cheek, eye sockets and ears. Similarly the arms, legs and torso are further represented hierarchically.

From the received skeletal information, posture detection block 204 calculates/determines the posture of infant 111, and thereafter identifies body parts of infant 111 that are of interest. Posture detection block 204 determines posture from the relative positions of the segmented body parts. Posture detection block 204 constructs segmented body parts from the extracted skeleton information. For example, after the first level segmentation using well known algorithms, the head, the torso, arms and legs are identified, as noted above. Once the head is identified, posture detection block 204 further segments the head to identify the nose, chin and forehead, as also noted above. The line joining the center of the forehead and the chin provides one vector and the line splitting the torso in two halves (left and right) provides another vector. The angle between two vectors is related to the bending angle of the neck. Posture detection block 204 may employ machine learning algorithms to perform the operations noted above.

In an alternative implementation, skeletal information is used as an input to a neural network or a support vector machine to implement a machine learning algorithm. The machine learning algorithm is trained using skeletal structures of large number of babies and simulation dolls with the information of whether the corresponding position is safe or not along with the name/id of the position. During normal operation, the unique name/id of the position and the safety are obtained as outputs. In addition, a provision is made for parents to willingly share information collected infield from the sensors on their babies. The processed information is used to train the machine learning algorithms further with the help of medical experts who help to classify the positions as safe or unsafe. Such an implementation provides scalability for including hitherto not-classified postures which may be classified as safe/unsafe based on the recommendations of medical experts.

In an embodiment, posture detection block 204 determines if infant 111 is lying belly-up, belly-down or sideways using the following techniques. The posture of the baby (infant 111) is declared to be belly-up or belly-down when the width of the torso region in the image is comparable to the head and when the average depth of the torso is nearly equal to or below the average depth of the head within a preset threshold. Otherwise, the baby posture is declared to be lying sideways. When the hips are facing up in belly-down position, the depth contours in the 3D image have a distinguishable maximum in the lower part of the torso. Posture detection block 204 uses such information to identify and segment the hips from the torso. If the hips are identified during the segmentation and are facing up, posture detection block 204 determines that the position is belly-down. Otherwise, the baby posture is declared to be belly-up.

Posture detection block 204 forwards the detected posture to posture monitoring block 205.

Figure 3:
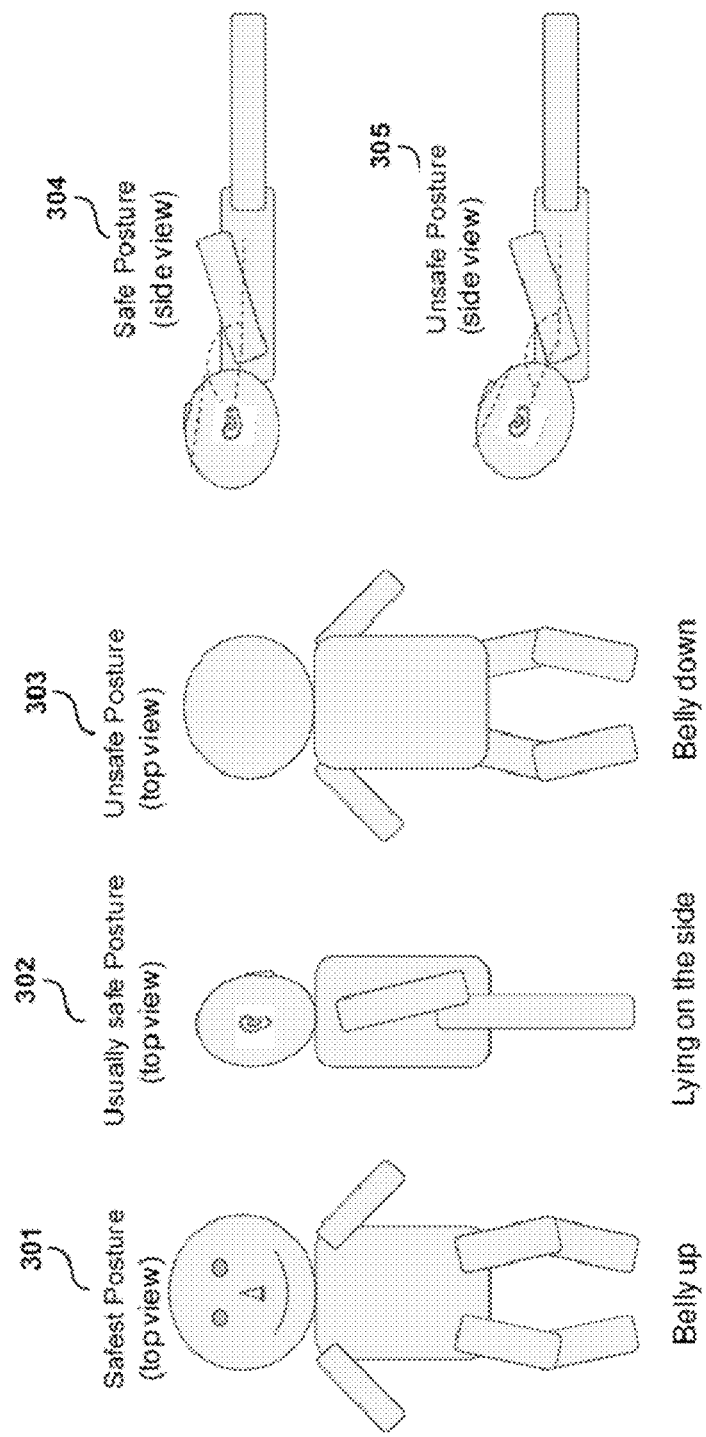
FIG. 3 shows diagrams of example safe and unsafe sleeping postures of an infant, in an embodiment of the present disclosure.
Figure 4:
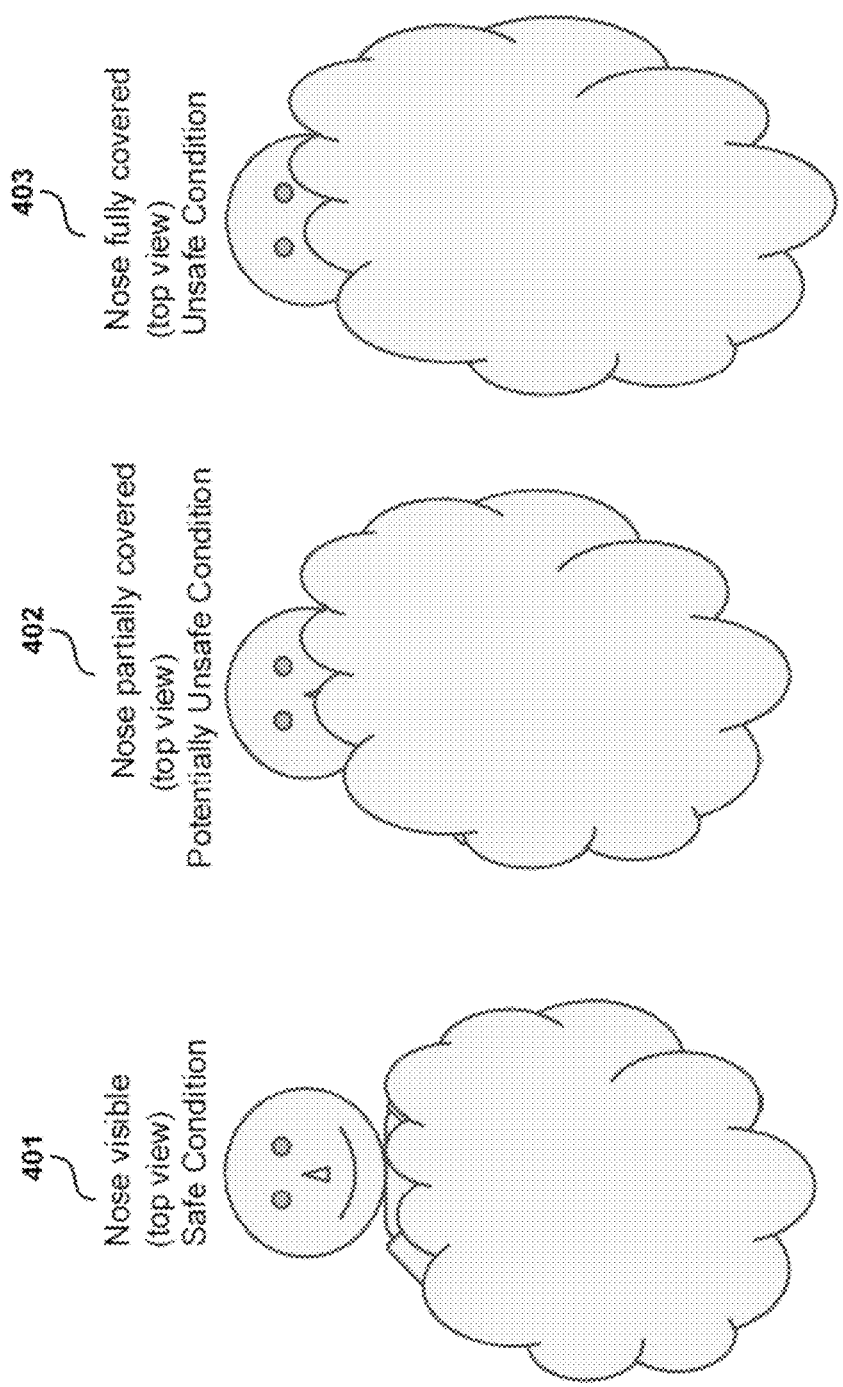
FIG. 4 shows diagrams of example safe and unsafe conditions of an infant, in an embodiment of the present disclosure.

From the received posture, posture monitoring block 205 determines if the infant posture is safe or not, or if the nose of the infant is not seen (for example, nose of the infant is not seen due to infant posture that is not safe or due to covering by blanket as indicated in FIGS. 3 and 4, described further below). If infant posture is determined as not safe or the nose is not seen, then alert generation block 206 generates and sends alerts to remote computing device 106.

FIG. 3 depicts diagrams illustrating examples of safe and unsafe postures of infant 111 as determined by posture monitoring block 205. Posture 301 showing a top view of infant 111 lying belly-up is deemed as the safest posture. Posture 302 showing a top view of infant 111 lying on its side is deemed as a "usually safe" posture. Posture 303 showing a top view of the infant 111 lying belly-down is deemed as an unsafe posture. Posture 304 showing a side view of the infant lying with head along the axis of the body is deemed as a safe posture. Posture 305 showing a side view of the infant lying with head tilted with respect to the axis of the body is deemed as an unsafe posture.

FIG. 4 depicts diagrams illustrating examples of safe and unsafe conditions with respect to infant 111, as determined by posture monitoring block 205. Position 401 shows a top view of the infant lying with nose not covered by a blanket (nose fully visible), and is deemed to be a safe condition. Position 402 shows a top view of the infant lying with nose partially covered by a blanket (nose partially visible), and is deemed as a potentially unsafe position. Position 403 shows a top view of the infant lying with nose covered by a blanket (nose fully covered), and is deemed as an unsafe position.

Figure 5:
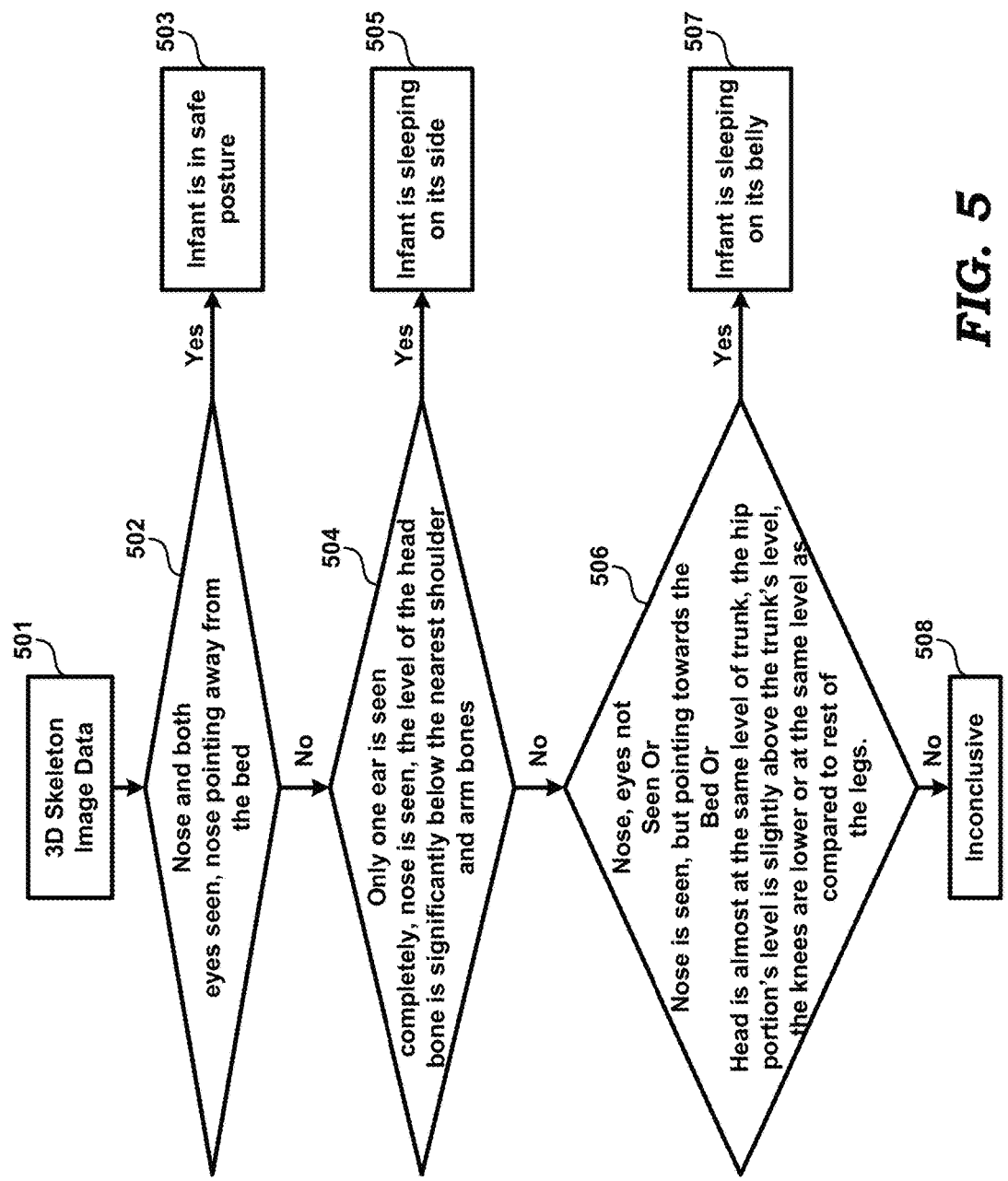
FIG. 5 is a flowchart illustrating the manner in which safe and unsafe postures of an infant are determined, in an embodiment of the present disclosure.

FIG. 5 is a flowchart illustrating a method for detection of safe and unsafe postures of infant 111. The skeletal information (3D skeleton image date 501) extracted by skeletal information extracting block 203 (of FIG. 2) is analyzed for angles between various bones, and angles that various bones make with the surroundings to obtain position and posture of the infant. Skeletal information 501, thus obtained, is provided as an input to posture monitoring block 205 to determine if infant postures are safe or not.

In step 502, posture monitoring block 205 determines if the nose and both eyes of infant 111 are visible and also if the nose is pointing away (e.g., upwards) from bed/crib 101. If the determination is positive, posture monitoring block 205 concludes (as indicated by box 503) that the infant is lying in a safe posture (for example, posture 301 of FIG. 3), as indicated by block 503. However, if the determination is negative, the method proceeds to step 504.

In step 504, posture monitoring block 205 determines if only one ear is seen completely, and if nose is seen and if the level of the head bone is significantly below the nearest shoulder and arm bones. If the determination is positive, then posture monitoring block 205 concludes (indicated in block 505) that infant 111 is sleeping on its side (for example, as in posture 302). If the determination is negative, the method proceeds to step 506.

In step 506, posture monitoring block 205 determines if the nose and eyes of infant 111 are not seen, or if nose is seen but pointing towards bed/crib 101, or if head is almost at the same level of torso, and the level of hip portion is slightly above the level of torso and the knees are lower or at same level as compared to legs. Posture monitoring block can make a determination of whether the nose is pointing towards the crib 101 in the following manner. The centroid of the head part of the skeleton is joined with the nose to form a line. If the point at which the line intersects the plane of the crib is nearer to the nose than to the centroid of the head, the nose is pointing down. Otherwise, it is determined as pointing up. If the line is nearly parallel (within a preset threshold of angle between the line and the plane), the nose is determined as pointing sideways.

If the determination of step 506 is positive, then posture monitoring block 205 concludes (in block 507) that infant 111 is lying with belly down (for example, as in posture 303).

If none of the conditions 502, 504 and 506 is satisfied, posture monitoring block 205 determines that no conclusion can be made (indicated in block 508), and alert generation block 206 sends a message to remote device 106 indicating that the infant monitoring system is not able to determine if the infant is in a safe posture or not.

Although not indicated in FIG. 5, the steps of the flowchart of FIG. 5 may be performed repeatedly at pre-determined intervals.

Based on the determined posture and/or condition of infant 111, alert generation block 206 sends alerts/alerts to the remote computing device 106. The alerts may be sent by a transceiver contained in infant monitoring system 100 in the form of a wireless signal. Alternatively, or in addition, the signal may be an audible sound that may be generated for example by a buzzer controlled by alert generation block 206.

Some of the examples when alerts are sent to remote computing device 106 are noted below:

(a) When the body of the infant is curved such that the neck is bent over the chest, alert generation block 206 sends an alert to the remote computing device 106 indicating the unsafe sleep posture. Skeletal information extraction block 203 extracts the skeletal information and posture detection block 204 calculates the angle between the head bone and spine by using the dot product of the two corresponding vectors and thereafter performs the inverse cosine to obtain a resultant angle (angle of tilt). When the angle of tilt is between 180° and 170° (both inclusive), posture monitoring block 205 determines the posture as safe (e.g., as in posture 304 of FIG. 3). When the resultant angle is lesser than 170 degrees, posture monitoring block 205 determines that the posture is not safe (for example, posture is as in posture 305 of FIG. 3). It is noted that according to recommended medical practice, currently the allowable window for angle of tilt is 10 degrees from the ideal resultant angle of 180°. Accordingly, posture determining block 205 determines the posture as not safe when the angle of tilt is lesser than 170 degrees. This allowable window for angle of tilt can be changed per doctor's recommendations. An alert is sent by alert generation block 206 to remote computing device 106 when the posture is not safe.

(b) When the infant has turned over with belly down (for example, as in posture 303) or is sleeping on its side (for example, as in posture 302), there is a risk of SIDS (Sudden Infant Death Syndrome) when certain kinds of bed 101 are used. Accordingly, an alert is sent by alert generation block 206 to remote computing device 106 indicating that the posture is unsafe.

(c) When the face of infant 111 is covered (e.g., by a blanket), posture monitoring block 205 determines that nose of the infant is not present in the features detected by posture detection block 205. Accordingly, an alert is sent by alert generation block 206 to remote computing device 106 indicating that there is a risk of SIDS since the position is not safe.

Posture monitoring system 200 also ascertains if cradle 190 has been setup in a safe recommended manner by comparing the setup against the ideal setup, and sends alerts to remote computing device 106 when an infant is left in a cradle that is not setup in a safe recommended manner. In an embodiment, the normal safe setup of the cradle is recorded as a reference 3D image in the factory during test. During operation, the cradle's 3D image scan is checked to compare against the factory setup to determine safety.

4. Activity Monitoring Sub-System

Figure 6A:
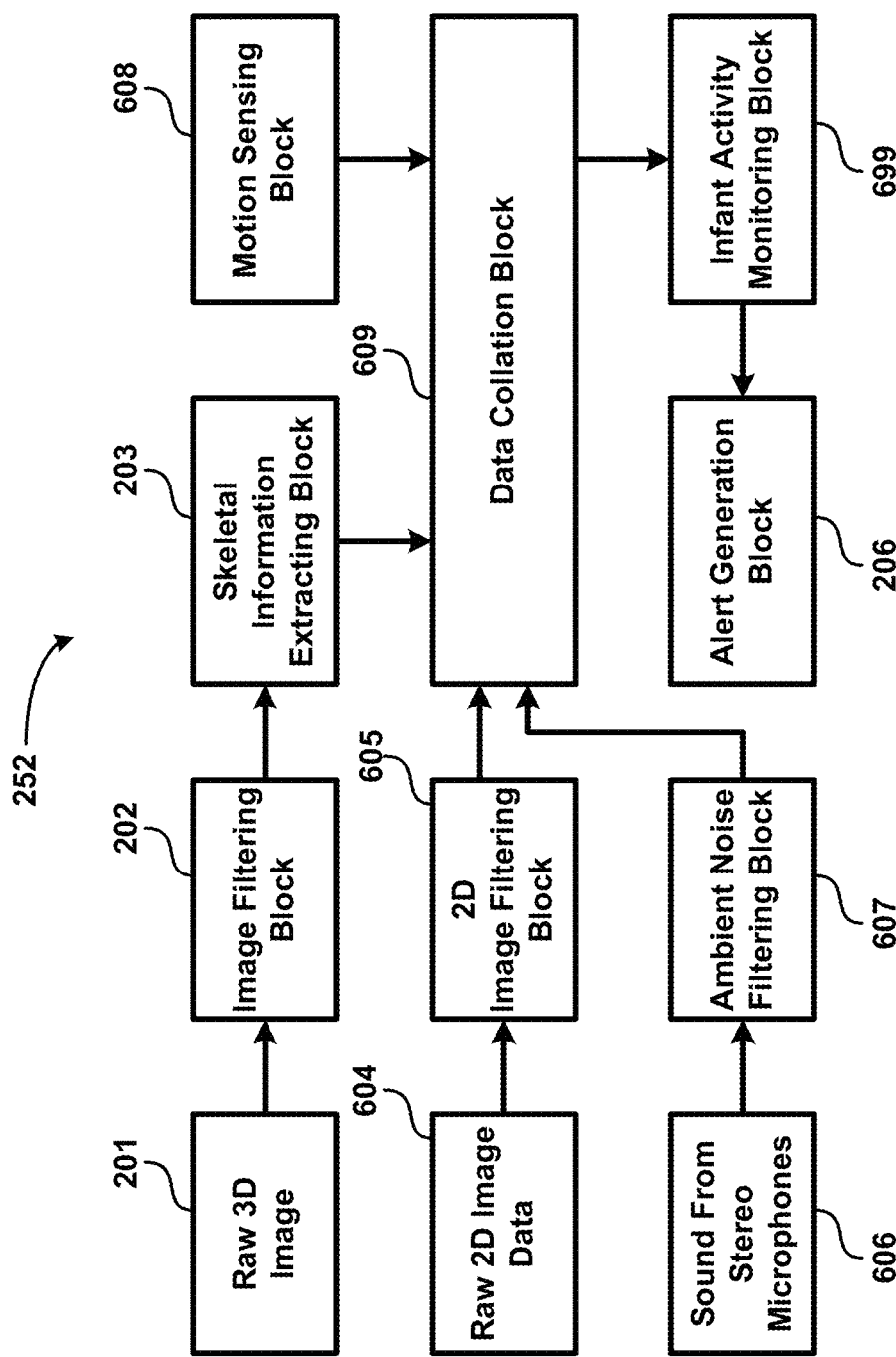
FIG. 6A is a block diagram of an activity monitoring sub-system, in an embodiment of the present disclosure.

FIG. 6A is a block diagram of an activity monitoring sub-system 252 in an embodiment of the present disclosure. is shown containing image filtering block 202, skeletal information extraction block 203, motion sensing block 608, 2D image filtering block 605, ambient noise filtering block 607, infant activity monitoring block 699 and alert generation block 206. It is noted that the operations of blocks 202, 605, 607 and 608 may be synchronized with respect to each other (i.e., performed substantially concurrently), such that the corresponding data (raw 3D image 201, raw 2D image data 604, sound 606, and motion) correspond to a same time interval or time instant.

Image filtering block 202 filters out pixels with low amplitude and high noise from raw 3D image 201, as also noted above. Then, skeletal information extracting block 203 extracts skeletal information from the filtered 3D image data, and provides the skeletal information as input to data collation block 609.

2D Image filtering block 605 determines if the eyes of infant 111 are open or closed based on raw 2D image data 604. As is well known in the relevant arts, a 3D camera provides x, y, z, and I for each point (pixel) in the captured image, wherein x, y and z refer to the 3 direction coordinates, and (I) is the intensity at the point. As also noted above, a 2D image is the intensity (I) portion (minus the location coordinates) obtained by the 3D camera. Raw 3D image 201 and raw 2D image data 604 are obtained simultaneously, i.e., from the same instance of illumination of the scene in the field of view 105 of 3D camera 102. After segmentation, 2D image filtering block 605 identifies the head of the infant, and calculates the approximate location of the eyes. In raw 2D image data 604, 2D image filtering block 605 the eye area is used as an input to a machine learning algorithm (assumed to be part of 2D image filtering block 605). The determination made by 2D image filtering block 605 is provided as input to data collation block 609.

Ambient noise filtering block 607 receives electrical (e.g., digital) representation of the sound/noises (606) received by the pair of stereo microphones 103 (FIG. 1). Ambient noise filtering block 607 filters ambient noise from sound 606 (obtained at the time of capturing of 3D image 201 and 2D image 604, or in a time interval straddling the instants at which images 201 and 604 are obtained) captured by stereo microphones 103 and extracts sounds generated by infant 111. Since stereo microphones are used, the difference in time of arrival of sounds at the two microphones can be used to judge the direction of the source of the sound. Any sound that whose time-of-arrival disparity is different from a reference disparity beyond a set threshold is filtered out. Ambient noise filtering block 607 provides the extracted sounds as inputs to data collation block 609.

Motion sensing block 608 includes one or more MEMS (micro electromechanical system) sensor (e.g., accelerometer 104 of FIG. 1) that is/are capable of sensing the motion of the infant. Motion sensor block 608 may filter certain specific frequencies. Such filtering helps in reducing the effects of cradle (or crib) motion on infant motion. The outputs of the sensor(s) are provided as input to data collation block 609.

Figure 6B:
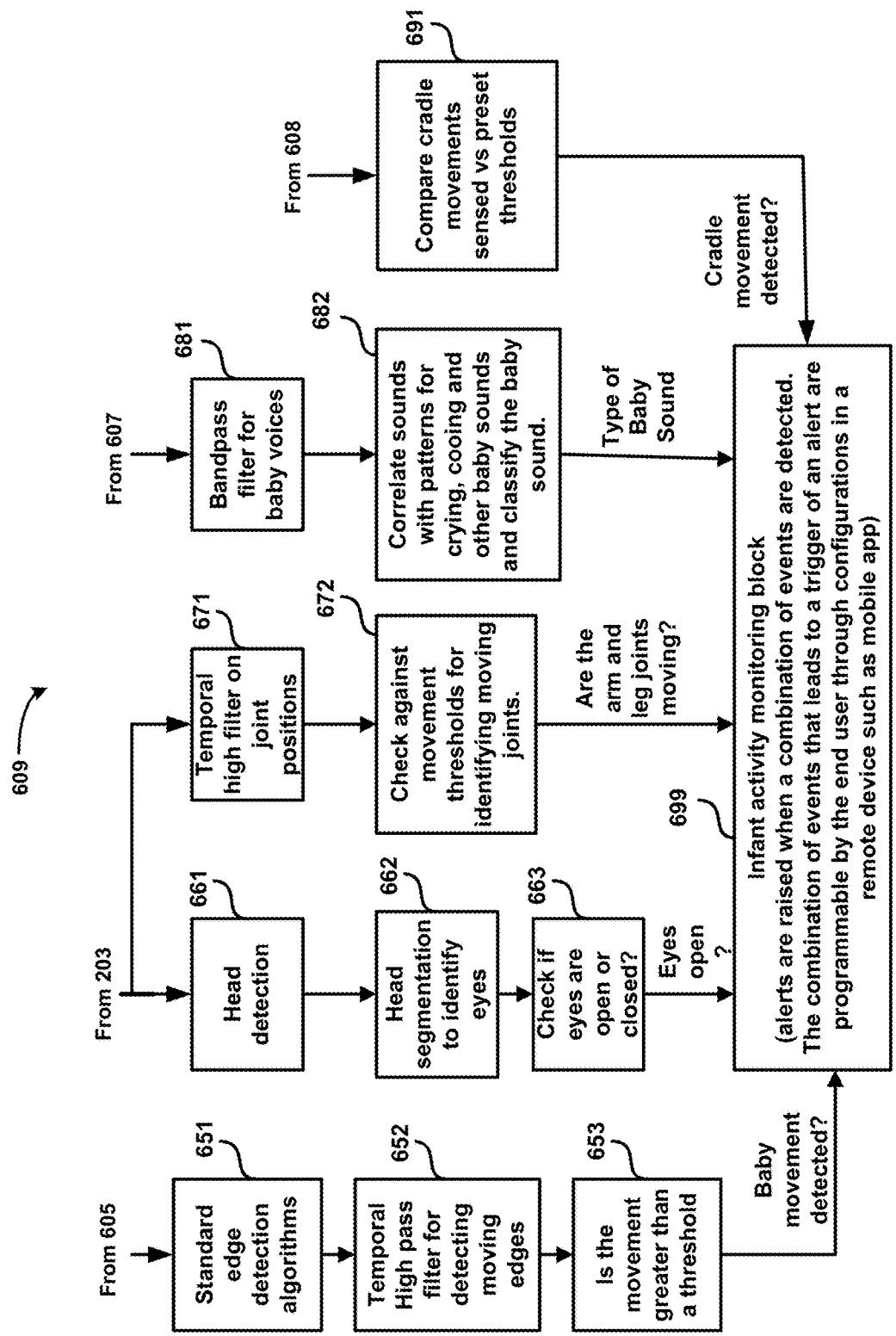
FIG. 6B is a block diagram of sub-blocks of a data collation block, in an embodiment of the present disclosure.

Data collation block 609 collates outputs from skeletal information extracting block 203, image filtering block 605, ambient noise filtering block 607 and motion sensing block 608. FIG. 6B shows the sub-blocks of data collation block 609 in an embodiment.

Block 651 receives the outputs of block 605 (FIG. 6A), and applies well known edge detection algorithms to detect edges in the images being processed. Block 652 performs temporal high-pass filtering on the output of block 651 to detect moving edges in the image. Block 653 processes the outputs of block 652 to determine if the movement of edges is greater than a pre-determined threshold.

Block 661 receives the outputs of block 203 (FIG. 6A), and detects the position of the head from the skeleton using machine learning based algorithms and/or deterministic approaches. Block 662 operates to segment the head (detected by block 662) to identify eyes, nose, forehead, chin and ears through the use of machine learning based algorithms. Block 663 operates on the output of block 662 to determine if the eyes are open or closed.

The manner in which block 663 determines if the eyes are open or closed in the following manner, in an embodiment of the present disclosure. Once the segmentation is done to locate the eyes, a spatial differential filter is applied to the 2d images (monochrome intensity images obtained from the 3D camera) around the area of the eyes. Areas of high contrast are represented by higher values in the filtered image. Closed eyes have a lower overall contrast as compared to eyes that are open. In a deterministic algorithm employed by bock 663, a preset threshold on the filtered image is used to determine if the eyes are closed or open.

In an alternative embodiment, block 663 employs machine learning algorithms. In such an embodiment, the filtered image is spatial decimated (averaged and decimated) and fed directly as input to a trained neural network or deep learning network to classify the image as eyes closed or open.

Block 671 receives the outputs of block 203 (FIG. 6A), and applies temporal high-pass filtering on positions of joints of arms and legs from the skeletal information received from block 203. Block 672 compares the movement of joints (as received from block 671) against a pre-determined threshold to determine if the quantum of movement of the joint(s) is sufficient to be classified as real motion. Block 672 thus determines if the joints in the arm and legs are moving or not.

Block 681 receives the outputs of block 607 (FIG. 6A) and applies band-pass filtering to remove sounds/noises other than baby voices. Block 682 operates on the output of block 681 to correlate the baby voices received with patterns for crying, cooing and other baby sounds, and classifies the baby sounds. Block 682 may employ machine learning algorithms.

After the filtering in block 681, in a deterministic algorithm, block 682 computes a floating point GCD (Greatest common divisor) of the top N frequency components that contain more than 90% of the power to identify the fundamental component. N may be a preset number between 5 and 20. Block 682 then applies further low-pass filtering to the GCD frequency value. Block 682 correlates the output of the low pass filter with typical temporal frequency profiles that represent baby cry. A high correlation indicates that the baby is crying. The typical temporal frequency profiles that represent cry can be pre-programmed in infant monitoring system 100, or provided (e.g., via remote device 106) as an update as and when more such patterns are learnt. In a machine learning based approach, block 682 windows (with last M samples where M is a preset number) the output of the low pass filter, and provides the window as an input to a trained neural or a deep learning network directly to assess if the baby is crying. Block 682 provides the classified baby sounds as an output.

Block 691 receives the output of block 608 (FIG. 6B), and compares cradle (101 of FIG. 1) movements (as identified by block 608) against preset thresholds. If the movements are greater than the preset thresholds, block 691 determines that cradle movement is present.

Infant activity monitoring block 699 operates to detect whether infant 111 is asleep or awake, and to detect active movements of infant 111, based on the data collated by data collation block 609. Infant activity monitoring block 699 monitors the following parameters:

(a) Whether eyes of infant 111 are open for a significant period of time.

(b) Whether infant 111 is crying.
(c) Whether active movements of infant 111 are seen for a significant period of time.
(d) Whether infant 111 is in a standing or a sitting position in crib 101. Such a condition can be determined by block 699 by checking, once the segmentation is done, if the head is above the torso and the legs beyond a threshold.

With respect to (b) above, audio data after filtering the ambient noise (i.e., the output of block 607) is fed to a band pass filter (not shown) to isolate human baby voices. After the band pass filter, the audio data is chopped into intervals corresponding to one-second durations and fed to a machine learning algorithm to assess if the sound is a crying sound.

Infant activity monitoring block 699 indicates the above activities to alert generation block 206 (FIG. 6A). Alert generation block 206 sends alerts to remote computing device 106 if/when output of infant activity monitoring block 699 indicates one or more of the following:
(a) eyes of infant are open for a significant period of time
(b) infant is crying
(c) infant is standing up/sitting in crib 101
(d) active movements of the infant are observed for a significant period of time.

Such alerts may be very critical information to the parents, especially in certain types of cradles which are not designed to be safe when the baby starts to sit, or when bed 101 is not designed to have safety features against baby crawling/rolling out and falling out of the bed (on such beds, it is particularly important to know if the baby is awake and moving).

Stereo microphones 103 include microphone arrays (a minimum of two). Use of microphone arrays enables localizing of sounds to their origin/source. Also, by correlating the sounds with raw 3D image of the face of infant, it is possible to determine if the infant is actually making the sounds or if stereo microphones 103 are picking up sounds other than the infant's from the environment.

5. Breath Rate Monitoring Sub-System

Figure 7:
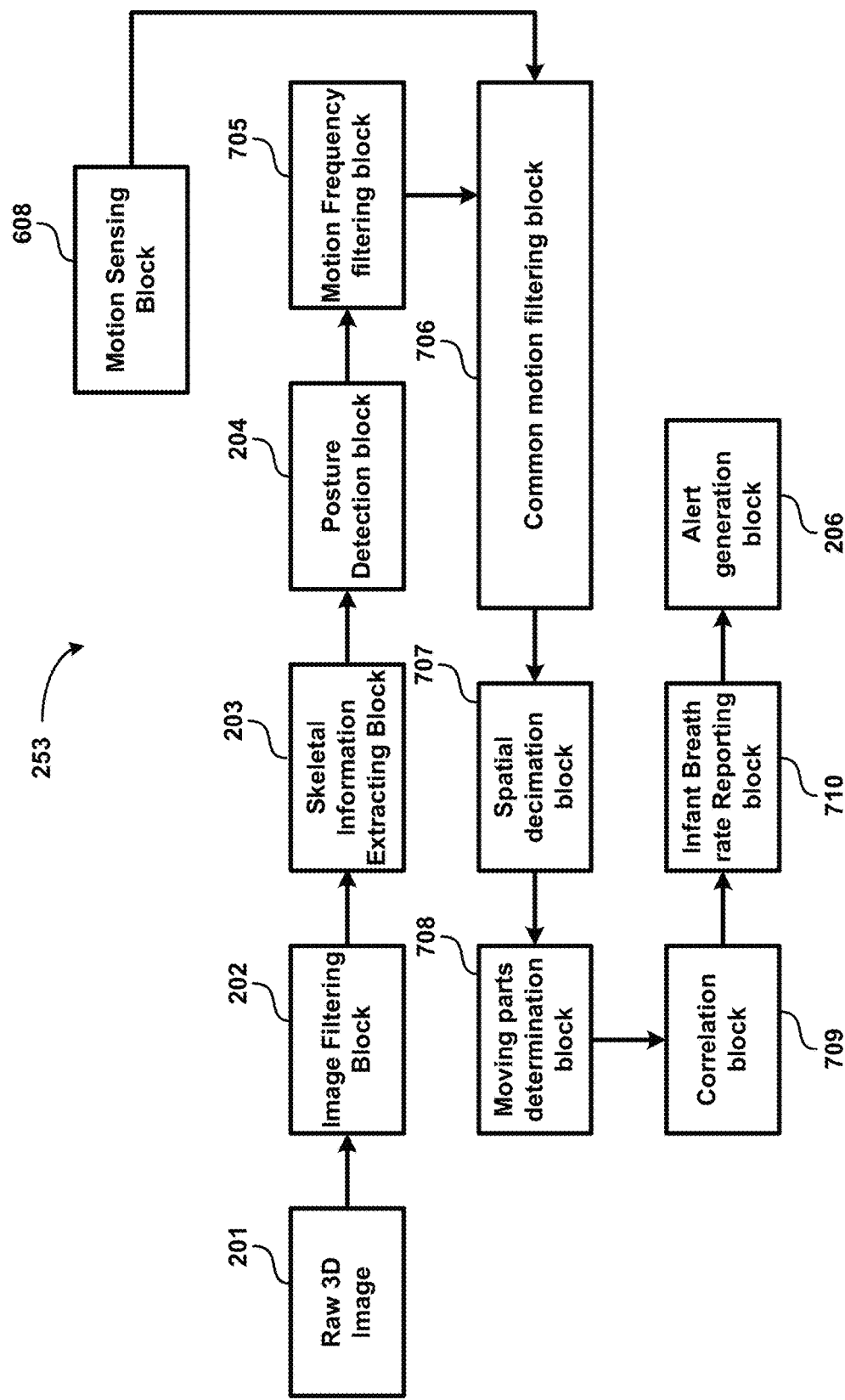
FIG. 7 is a block diagram of a breath rate monitoring sub-system, in an embodiment of the present disclosure.

FIG. 7 is a block diagram of a breath rate monitoring system in an embodiment of the present disclosure. Breath rate monitoring sub-system 253 is shown containing image filtering block 202, skeletal information extraction block 203, posture detection block 204, motion frequency filtering block 705, motion sensing block 608, common motion filtering block 706, spatial decimation block 707, moving parts determination block 708, correlation block 709, infant breath rate reporting block 710 and alert generation block 206.

Image filtering block 202 filters out pixel values having low amplitude and high noise from raw 3D image 201, as also noted above. Then, skeletal information extraction block 203 extracts skeletal information from the filtered 3D image data. The skeleton is used to identify various parts of the body of infant 111. Once the body parts are identified, the raw 3D image near the regions of interest (e.g., torso in this case) is used to detect motion.

Since breath-rate detection algorithm depends on the identification of the torso and the belly, the above-described first/top level of segmentation is sufficient for breath-rate algorithm. From the skeletal information, posture detection block 204 detects posture of the infant (as noted in sections above) and identifies body parts that are of interest. Infant posture can be used to better identify body parts that exhibit breathing motion. For example, in measuring infant's breath rate, one body part of interest is the torso of the infant since the torso is the part of the body that moves the maximum when the infant breathes. Torso, as is well known, is that part of the body of a human or animal that contains the chest, belly and abdomen.

Posture detection block 204 determines the posture of the infant as described above. The outputs of posture detection block 204 include an ID (identifier) of the posture. Using the ID, posture detection block 204 does a look-up through a pre-programmed look-up table to obtain the approximate position and orientation of various parts of the body, for example, position of the chest, torso and the neck (areas that are important for breath rate detection) and the remaining areas that do not exhibit motion due to breath. The remaining areas along with the background (cradle) are used for detection of common motion due to rocking (in common motion filtering block 705, described below). The frequencies of rocking thus obtained are filtered out from the frequency spectrum obtained from the areas of interest for breath. This operation results in a signal that is only representative of breath.

Based on the skeletal information and the outputs of posture detection block 204, motion frequency filtering block 705 filters out frequencies in the 3D images (i.e., in a sequence of successive 3D images obtained from block 201) that do not match breath rate. Then, from the filtered 3D image information, common motion filtering block 706 further filters out common motion using data from motion sensing block 608 and any background movement present in the outputs of posture detection block 204. Common motion refers to motion components that are common in both the region of interest (torso of the infant) as well as background objects. For example, when cradle 190 is in rocking (oscillating) mode, there may be motion components in the region of interest that are due to such rocking motion, and not breathing.

Motion sensor block 608 is used to detect the frequencies of external oscillation which are not due to the infant breathing. A notch filter may be used to filter out specific oscillation frequencies. Such filtering helps in reducing the effects of cradle (or crib) motion on breath rate sensing. A band-pass filter is used to remove noise that is out of band and to obtain the frequencies of interest corresponding to normal breath rates of infants.

Thereafter, spatial decimation block 707 spatially decimates skeletal information of image filtered by common motion filtering block 706. Spatial decimation refers to spatial low-pass filtering followed by discarding some pixels and keeping only every $n^{th}$ pixel (n being a convenient integer) in both horizontal and vertical directions. From spatially decimated image of the spatial decimation block 707, moving parts determination block 708 determines moving parts in the 3D image. That a body part is moving can be determined based on a comparison of the location of the part in successive frames. Regular oscillating movement can be detected by observing the displacements from a mean position. In the detected moving parts, correlation block 709 correlates adjacent moving parts and thereafter groups such adjacent moving parts of the 3D image when the correlation is good. Correlation refers to a determination of how closely motions of a pair of moving parts resemble each other. Greater correlation implies that the moving parts are located close to or next to each other.

Infant breath rate reporting block 710 determines the breath rate of infant 111 by averaging the motion of the grouped moving parts. Alert generation block 206 generates and sends alerts to remote computing device 106 when the breath rate reported is out of the range of normal breathing for infants. For example, if the breath rate reported is too high or low (as specified by corresponding high and low thresholds), alert generation block 206 generates and sends an alert. Additionally, if breath rate is detected as zero for a significant duration, alert generation block 206 generates and sends a high priority alert indicating detection of a possible sleep apnea event.

It may be appreciated that breath rate monitoring system 700 is a contactless breath rate monitoring system for infants.

6. Heart Rate Monitoring Sub-System

Figure 8:
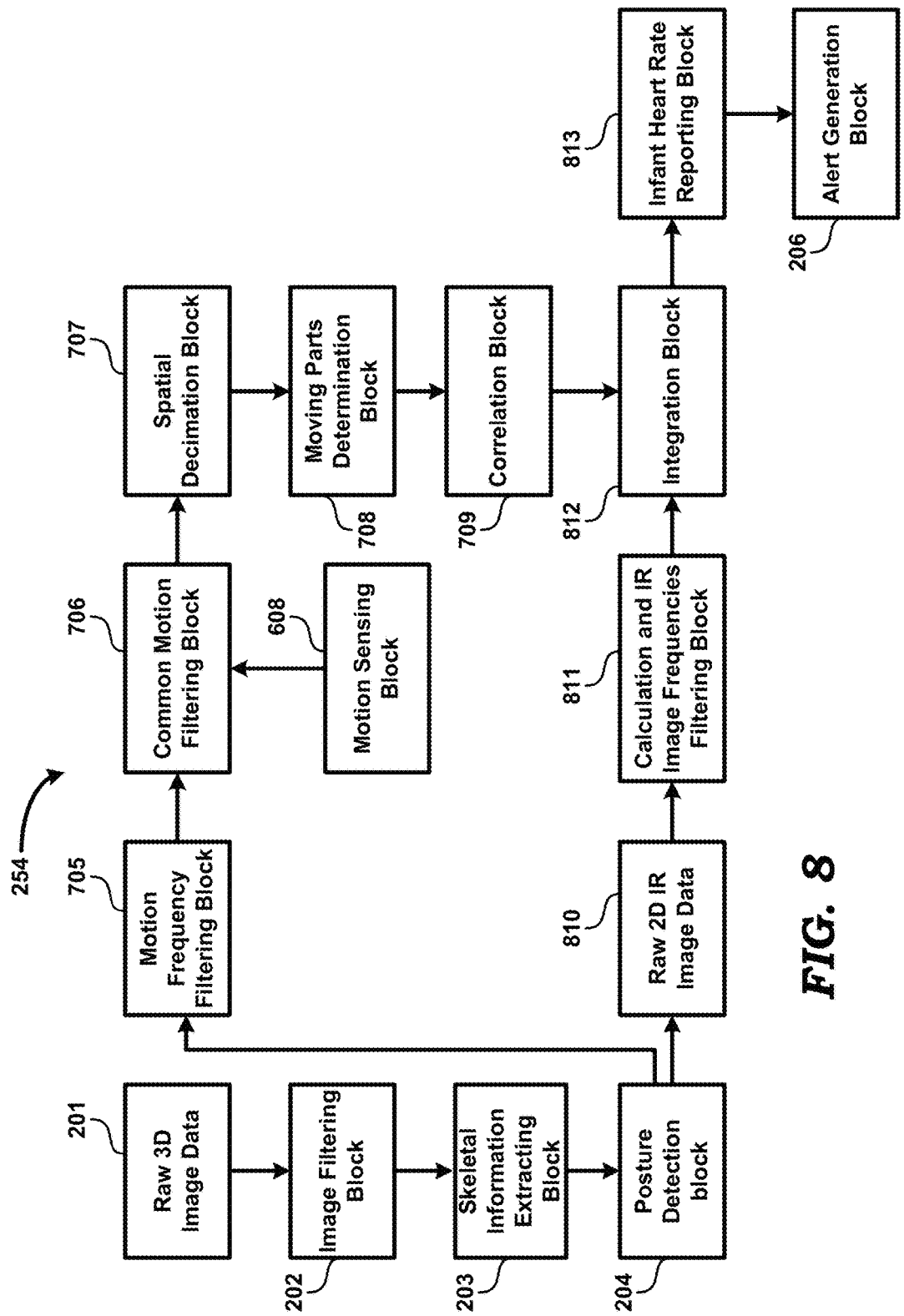
FIG. 8 is a block diagram of a heart rate monitoring sub-system, in an embodiment of the present disclosure.

FIG. 8 is a block diagram of a heart rate monitoring system in an embodiment of the present invention. Heart rate monitoring sub-system 254 is shown containing, image filtering block 202, skeletal information extraction block 203, posture detection block 204, motion frequency filtering block 705, common motion filtering block 706, motion sensing block 608, spatial decimation block 707, moving parts determination block 708, correlation block 709, raw 2D image data block 604, calculation and image frequencies filtering block 811, integration block 812, infant heart rate reporting block 813 and alert generation block 206. It is noted that the operations of blocks 811 and 705 may be synchronized with respect to each other (i.e., performed substantially concurrently), such that the blocks 811 and 705 operate on outputs of posture detection block 204 of a same time interval or time instant.

Image filtering block 202 filters pixels with low amplitude and high noise from raw 3D image 201, as also noted above. Then, skeletal information extraction block 203 extracts skeletal information from the filtered 3D image data.

From the skeletal information, posture detection block 204 calculates and detects infant posture and thereafter identifies body parts that are of interest. Infant posture can be used to better identify body parts that exhibit signs of heartbeat. For example, in measuring infant's heart rate, body parts of interest are the face and the neck of infant since the shade of the face changes slightly in the 3D image 201 and there are minor pulse movements around the neck. Such minor pulse movements are detected due to changes in distance information of the raw 3D image 201. Posture detection block 204 also generates raw 2D image 604 from the received skeletal information. Raw 2D image data 604 contains the intensity (I) component alone (i.e., no x, y, z coordinates) the image data received from block skeletal information extraction block 203.

Motion frequency filtering block 705 receives the output (i.e., identified body parts of interest) of posture detection block 204, and filters out frequencies in the received output that do not match heart rate. Then, from the filtered skeletal information, common motion filtering block 706 further filters out common motion using data from motion sensing block 608 and background movement captured from 3D camera 102. One or more MEMS (micro-electromechanical systems) motion sensors (e.g., accelerometer 104 shown FIG. 1) is used to detect the frequencies of external oscillation (i.e., frequencies that are not due to heartbeats of infant 111). A notch filter may be used to filter specific oscillation frequencies. Such filtering helps in reducing the effects of cradle motion on heart rate sensing. A band-pass filter is used to remove noise that is out of band and get the frequencies of interest corresponding to normal heart rates of infants.

Thereafter, spatial decimation block 707 spatially decimates skeletal information of image filtered by common motion filtering block 706. From the spatially decimated image generated by spatial decimation block 707, moving parts determination block 708 determines moving parts in the image. Correlation block 709 correlates adjacent moving parts in the moving parts determined by block 708 and thereafter groups such adjacent moving parts when the correlation is good.

Thereafter, calculation and image frequencies filtering block 811 calculates scene-to-scene changes (i.e., differences between successive raw 2D images received) in the raw 2D image 604, and filters out frequencies in the raw 2D images that do not match (typical) heart rates of an infant. For example, from raw 2D image data 604, calculation and image frequencies filtering block 811 detects the darkening and lightening of skin tone (of skin of infant 111) synchronous with heartbeat. The rate at which the darkening and lightening of skin tone are generally the same as the heartbeat rate. It is noted that skin tone at all places with visible skin can be used for determining the heart rate. The skin tone from different visible areas is spatially averaged and is sent through a temporal band-pass filter to identify the rate of the heartbeat. Furthermore, calculation and image frequencies filtering block 811 uses band-pass filtering to filter out frequencies that do not correspond to normal heartbeat rates of infants.

Then, integration block 812 integrates the outputs of correlation block 709 and output of calculation and image frequencies filtering block 811 by weighting and combining correlated information (from correlation block 709) and calculated scene-to-scene information reflecting color changes (generated by block 811). Integration block 812 checks if the heart rate obtained from block 811 is close to the one obtained from 709 within a preset threshold. If the rates are very different, the heart rate obtained is discarded. In some cases, if only one of the two blocks out of 811 and 709 provide a detectable heart rate, the detected heart rate is used as output as it is. If the heart rate obtained from both the blocks is similar within threshold, output heart rate is a weighted average of the two rates where the weights will be preset.

Infant heart rate reporting block 813 receives the output of integration block 812, and determines the heart rate of infant 111 based on averaging motion of the grouped moving parts and calculated color changes determined by the other corresponding blocks as noted above.

Alert generation block 206 generates and sends alerts to remote computing device 106 if/when the heart rate determined by block 813 is out of the range of normal heart rate for infants. For example, if the heart rate reported is too high or low, alert generation block 206 generates and sends an alert.

It may be appreciated that heart rate monitoring system 800 is a contactless heart rate monitoring system for infants.

7. Insect Detection Sub-System

Figure 9:
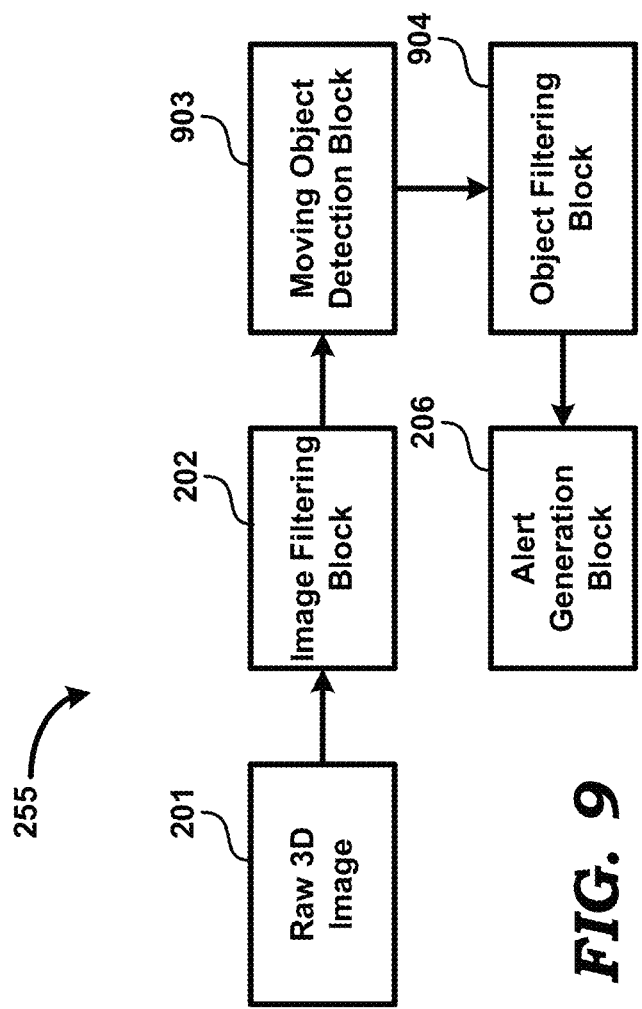
FIG. 9 is a block diagram of an insect detection sub-system, in an embodiment of the present disclosure.

FIG. 9 is a block diagram of an insect detection system in an embodiment of the present disclosure. Insect detection system 900 is shown containing image filtering block 202, moving object detection block 903, object filtering block 904 and alert generation 206.

Image filtering block 202 filters pixels with low amplitude and high noise from raw 3D image 201.

Moving object detection block 903 operates on the output of image filtering block 202, and detects any moving object that is close to infant 111, and between the camera and infant 111 in the FoV 105. As an example, an insect in FoV 105 can be detected as such moving object since it is between the background (e.g., crib 101) and 3D camera 102.

Then, object filtering block 904 filters out objects that are too large or too small to be insects (based on size), and further filters out objects having very regular and slow pattern of motion. For example, object filtering block 904 filters out objects such as large specks of dust. Random motion of insects versus more predictable motion of large specks of dust forms the basis of filtering out of objects other than insects by object filtering block 904.

Alert generation block 206, based on the output of object filtering block 904, generates and sends alerts to remote computing device 106 when any flying insect is detected close to infant 111.

Insect detecting system 900 may help in protecting infants from insect bites, especially mosquito bites causing diseases such as dengue, malaria, etc. An alert is sent out if any insects are detected near the infant. A count of the number of insects that are detected is also preserved along with corresponding time-stamps of when they were detected. Such data may help parents to take necessary actions to keep insects away and also used for further analysis. For example, dengue mosquitoes are more active during the day and a detection of mosquitoes during day time is likely to be indicative of the mosquito being a dengue mosquito.

Additional features of the present invention are briefly described below.

8. Hand Gesture Inputs

According to another aspect of the present invention, infant monitoring system 100 also enables hand gesture inputs and triggers switching on/off of lights on one or more portions of cradle 190, controlling of a music system (fitted in cradle 190) for entertainment of infants, etc. 3D camera 102 helps in detecting hand gesture inputs from a parent/caretaker and triggers actions corresponding to the hand gestures. For example, the following actions are triggered when a hand gesture is detected in front of 3D camera 102:
  (a) A gesture of opening of a hand is used to turn on, dim or brighten some display lights.
  (b) A gesture of hand swiping is used to change songs played in the music system in the cradle. For example, a gesture of hand swiping is used to change to previous/next song;
  (c) A gesture of rotation of hand in clockwise or anti-clockwise direction is used to change the volume of the music being played in the cradle;
  (d) A gesture of placing of a hand in front of the 3D camera stops rocking of the cradle by sending a stop signal to rocking system 107; and
  (e) A gesture of to-and-fro hand wave in the horizontal direction triggers the rocking system 107 to rock in the horizontal direction, and a gesture of to-and-fro hand wave in the vertical direction triggers the rocking system 107 to rock in the vertical direction.

It is noted that hand gesture recognition is well known in the relevant arts, and there are many well-known algorithms, some of which are described in the following references:
a) Hand gesture recognition based on shape parameters, authored by Meenakshi Panwar, published in Computing, Communication and Applications (ICCCA), 2012 International Conference, Date of Conference: 22-24 Feb. 2012;
b) A real time hand gesture recognition system using motion history image, authored by Chen-Chiung Hsieh, Dung-Hua Liou and David Lee, published in: Signal Processing Systems (ICSPS), 2010 2nd International Conference, Date of Conference: 5-7 Jul. 2010;
c) Survey on 3D Hand Gesture Recognition, authored by Hong Cheng, Lu Yang and Zicheng Liu, published in: IEEE Transactions on Circuits and Systems for Video Technology (Volume: 26, Issue: 9, September 2016), Page(s): 1659-1673, Date of Publication: 18 Aug. 2015.

9. Sound Inputs

Stereo microphones 103 use microphones (minimum of 2, for example 103A and 103B shown in FIG. 1) so that sounds can be localized to their source. Also, raw 3D image of the face of infant 111 enables determining whether infant is actually making sounds or if the stereo microphones are picking up sounds (noise, other than sounds made by infant 111) from the environment. Sounds made by infant 111 are used to trigger alerts or send commands to external rocking mechanism 107 connected to cradle 190. Some examples of alerts issued based on sounds made by infant 111 are noted below:

Crying sounds made by infant 111, in combination with other alerts (described above) generated based on the data from the 3D camera and motion sensor, are used to signal to the parents that the infant is awake and requires attention. If rocking mechanism 107 is connected to cradle 190, sounds made by the infant serve as input to the infant monitoring system 100 to cause infant monitoring system 100 to send a command to the rocking mechanism 107 to initiate rocking.

Loud external sounds such as horns, sound from falling objects, etc. can be detected, and can serve as inputs to infant monitoring system 100 to cause rocking mechanism 107 to initiate rocking.

The processing of various alerts (noted above) and control of remote computing device 106 is described in next.

10. Processing of Alerts and Information Related to Alerts and Infant Monitoring All the data from the various sensors such as motion sensor (for example, accelerometer 104), audio sensors (stereo microphones 103) and visual image sensor (3D camera 102) are gathered and processed locally by infant monitoring system 100, which may send only consolidated/processed information and alerts to remote computing device 106 (which may, for example, be a smartphone, tablet or a personal computer). The information sent to remote computing device 106 is made accessible in a user-friendly form using an application on the remote computing device 106. For critical events (e.g., an alert condition exits), all data from various sensors are recorded in infant monitoring system 100 before and after such event. The data is then sent to remote device 106, which can be used to analyze and review such events at a later point in time.

11. Implementation Details

Figure 10:
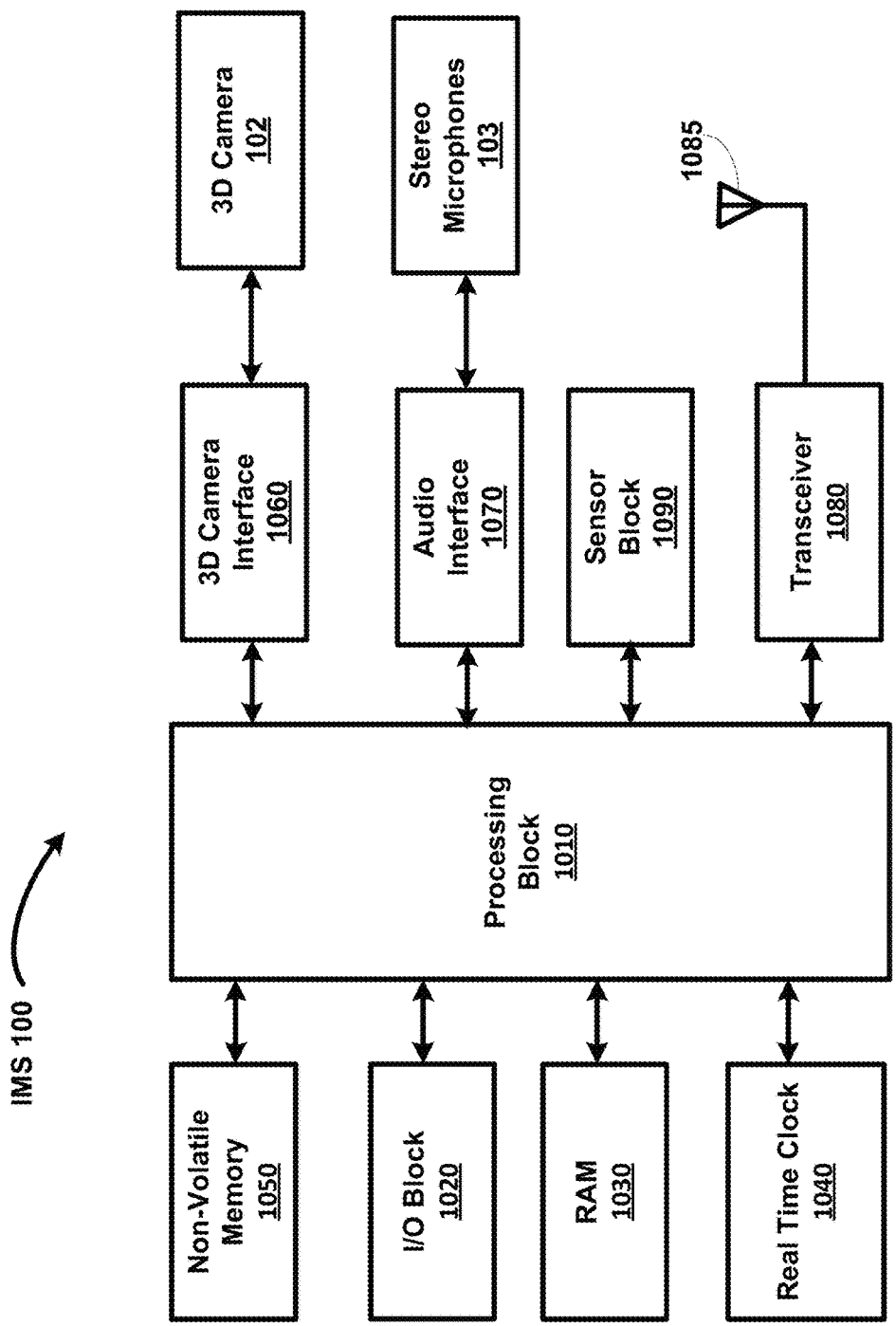
FIG. 10 is a block diagram illustrating the implementation details of an infant monitoring system in an embodiment of the present disclosure.

FIG. 10 is a block diagram showing the implementation details of infant monitoring system (IMS) 100 in an embodiment of the present disclosure. IMS 100 is shown containing processing block 1010, input/output (I/O) block 1020, random access memory (RAM) 1030, real-time clock (RTC) 1040, non-volatile memory 1050, 3D camera interface 1060, 3D camera 102, audio interface 1070, stereo microphones 103, transceiver 1080, sensor block 1090, and antenna 1085. A battery (not shown) may be used to provide power for operation of the various blocks of FIG. 10. Alternatively, the blocks may be powered by the output of a power supply (not shown) connected to mains power.

I/O block 1020 provides interfaces for user interaction with IMS 100, and includes input devices and output devices. The input devices may include a keypad, while the output devices may include a display.

RTC 1040 contains oscillator(s) for generation of clock signals required for operation of one or more of the other blocks of FIG. 10. In addition, RTC 1040 contains one or more timers for maintaining current time.

3D camera interface 1060 contains circuitry for processing the output of, as well as for controlling the operation of, 3D camera 102. 3D camera interface 1060 provides 3D image data generated by 3D camera 102 to processing block 1010.

Audio interface 1060 receives audio signals in analog form from one or more microphones in stereo microphones 103, converts the analog signals to digital data, and provides the digital data to processing block 1010.

Sensor block 1090 may contain one or more sensors such as accelerometer 104 (e.g., in MEMS form). Sensor block 1090 may process the signals generated by such sensors, and forward the processed signal in digital form to processing block 1010.

Antenna 795 operates to receive wireless signals (e.g., WiFi™ frames, Bluetooth™ signals, etc. for example from remote device 106 of FIG. 1), and provides the signals to transceiver 1080. Antenna 795 receives signals for transmission from transceiver 1080, and transmits the signals on a wireless medium.

Transceiver 1080 contains transmit and receive circuits. The transmit circuits receive data (e.g., alerts) to be transmitted from processing block 1010, modulate (e.g., according to WiFi™/Bluetooth™ standards) a carrier with the data and transmit the data on a wireless medium via antenna 1085. The receive circuits receive modulated carrier signals (e.g., according to WiFi™/Bluetooth™ standards) from the wireless medium via antenna 1085, demodulate the carrier, and forward data obtained by the demodulation to processing block 1010. The received data includes commands from remote device 106, updates to algorithms executed in infant monitoring system 100, etc.

Non-volatile memory 1050 is a non-transitory machine readable medium, and stores instructions, which when executed by processing block 1010, causes IMS 100 to operate as described in detail above. In particular, non-volatile memory 1050 stores instructions representing the various blocks (such as image filtering block 202, alert generation block 206, etc.) of FIG. 2 and FIGS. 6-9. The instructions, when executed by processing block 1010, enable IMS 100 to operate as described in detail above. The instructions may either be executed directly from non-volatile memory 1050 or be copied to RAM 1030 for execution.

RAM 1030 is a volatile random access memory, and may be used for storing instructions and data. RAM 730 and non-volatile memory 1050 (which may be implemented in the form of read-only memory/ROM/Flash) constitute computer program products or machine (or computer) readable medium, which are means for providing instructions to processing block 1010. Processing block 1010 may retrieve the instructions, and execute the instructions to provide several features of the present disclosure.

Processing block 1010 (or processor in general) may contain multiple processing units internally, with each processing unit potentially being designed for a specific task. Alternatively, processing block 1010 may contain only a single general-purpose processing unit. Processing block 1010 executes instructions (representing the various blocks of FIG. 2 and FIGS. 6A, 6B, 7-9) stored in non-volatile memory 1050 or RAM 1030 to enable IMS 1010 to operate according to several aspects of the present disclosure, described above in detail.

12. Conclusion

References throughout this specification to "one embodiment", "an embodiment", or similar language means that a particular feature, structure, or characteristic described in connection with the embodiment is included in at least one embodiment of the present invention. Thus, appearances of the phrases "in one embodiment", "in an embodiment" and similar language throughout this specification may, but do not necessarily, all refer to the same embodiment. The following examples pertain to above or further embodiments.

Example 1 corresponds to a monitoring system. The monitoring system includes a camera to generate images of an infant, a processing block to process one or more of the generated images and to identify a condition with respect to the infant, and an alert generator to cause generation of an alert signal if the identified condition warrants external notification. The camera, processing block and alert generator are part of a unit placed in the vicinity of said infant.

Example 2 corresponds to the monitoring system of example 1, in which the camera is implemented in the form of a 3D camera to generate the one or more images as one or more 3D (three-dimensional) images of the infant located in a field-of-view (FoV) of the 3D camera. The infant is placed on a stable surface within the FoV.

Example 3 corresponds to the monitoring system of example 1 or example 2, which further includes a motion sensor to generate motion signals representative of motion of the infant, and to generate filtered motion signals by filtering out the components of motion signals that are due to motion of the surface/platform on which the infant is placed.

Example 4 corresponds to the monitoring system of any of examples 1-3, in which the condition with respect to the infant is a posture of the infant.

Example 5 corresponds to the monitoring system of any of examples 1-4, wherein the processing block is operable to extract skeletal information of the infant from the one or more 3D images, determine body parts of interest from the skeletal information, and determine the posture of the infant from the body parts of interest. The posture may be one of a belly-up posture, a side posture, and a belly-down posture. A belly-up posture is one, in which the nose and both eyes of the infant are determined to be visible, and the nose of said infant is determined to point away from the surface on which the infant is placed. A side posture is one, in which only one ear of the infant is determined to be visible, and wherein the level of the head bone of the infant is determined to be below the nearest shoulder and arm bones of the infant. A belly-down posture is one, wherein the nose and eyes of the infant are determined not be visible, or wherein the nose is determined to be pointing towards the surface, or wherein the head of the infant is determined to be at the same level as the torso of the infant, and wherein the hip of the infant is above the torso of the infant, and wherein the knees of the infant are lower than or at the same level as the rest of the leg portion of the infant. The alert generator generates an alert signal if the processing block identifies the posture to be a belly-down posture.

Example 6 corresponds to the monitoring system of any of examples 1-5, in which extracting skeletal information, determining body part of interest and determining posture from body parts of interest employ machine learning algorithms.

Example 7 corresponds to the monitoring system of any of examples 1-3, in which the condition with respect to the infant is an activity state of the infant.

Example 8 corresponds to the monitoring system of any of examples 1-3 and 7, in which the monitoring system further includes stereo microphones to generate audio signals representative of sound in the vicinity of the infant. The stereo microphones contain a first microphone and a second microphone, the first microphone and the second microphone being positioned such that the infant lies in a line that passes through each of the first microphone and the second microphone. The processing block is further operable to extract skeletal information of the infant from the one or more 3D images, filter out ambient noise from the audio signals to generate filtered audio signals, determine if eyes of the infant are open by processing a 2D (2-dimensional) image obtained by retaining only the intensity components of pixels in one of more of the 3D images, collate data from the skeletal information, the filtered audio signals, the filtered motion signals, and ascertain the activity state from the collated data, wherein at least some operations of the ascertaining employs machine learning algorithms. The activity state may be one of a first state in which eyes of the infant are determined to be open for a period of time longer than a first threshold, a second state in which the infant is crying, a third state in which movements by the infant are determined to be present for a period of time longer than a second threshold, and a fourth state in which the infant is determined to be in a standing or a sitting position on the surface. The alert generator generates the alert signal upon ascertaining the activity states of the infant.

Example 9 corresponds to the monitoring system of any of examples 1-3, in which the condition with respect to the infant is breath rate of the infant.

Example 10 corresponds to the monitoring system of any of examples 1-3 and 9, in which the processing block is operable to extract skeletal information of the infant from the one or more 3D images, determine the posture of the infant from the skeletal information, identify, from the posture, body parts exhibiting breathing motion, wherein the body parts comprise the torso of the infant, filter out motion components in the motion of the torso that are due to motion of the surface to generate a filtered sequence of images, determine moving parts in the filtered sequence, wherein the moving parts includes the torso of the infant, generate a grouped moving parts based on correlating motion of adjacent parts in the moving parts, and determine the breath rate of the infant from the grouped moving parts. The alert generator generates the alert signal if the processing block determines that the breath rate falls outside of a pre-determined range.

Example 11 corresponds to the monitoring system of any of examples 1-2, in which the condition with respect to the infant is breath rate of the infant.

Example 12 corresponds to the monitoring system of any of examples 1-2 and 11, in the processing block is operable to processing block is operable to extract skeletal information of the infant from the one or more 3D images, determine the posture of the infant from the skeletal information, identify, from the posture, body parts exhibiting breathing motion, wherein the body parts comprise the face and the neck of the infant, filter out motion components in the motion of the face and neck that are due to motion of the surface to generate a filtered sequence of images and determine moving parts in the filtered sequence, wherein the moving parts includes the face and neck of the infant, generate a grouped moving parts based on correlating motion of adjacent parts in the moving parts, process scene-to-scene changes in a set of 2D (2-dimensional) images to detect darkening and lightening of skin tone of skin of the infant, wherein the set of 2D images are obtained by retaining only the intensity components of pixels in one of more of the 3D images, filter out frequencies in the scene-to-scene changes that fall outside of a normal range of frequencies of heartbeat of an infant, weighting and combining data representing the grouped moving parts and data representing the scene-to-scene changes, and determine the heart rate based on an average motion of the grouped moving parts and the detection of darkening and lightening of skin tone. The alert generator generates an alert signal if the processing block determines that the heartbeat falls outside a normal range.

Example 13 corresponds to the monitoring system of any of examples 1-2, in which the condition with respect to infant is the presence of an insect in the vicinity of the infant.

Example 14 corresponds to the monitoring system of any of examples 1-2 and 13, in which the processing block is operable to detect, by processing the one or more 3D images, presence of a moving object between the 3D camera and the infant, filtering out, from the one or more 3D images, objects that have a size that is outside of a normal range of sizes for insects, filtering out, from the one or more 3D images, moving objects that have a motion that is determined not to resemble that of an insect. The alert generator generates the alert signal if the processing block detects presence of an insect.

Example 15 corresponds to the monitoring system of example 1 or example 2, in which the alert signal is transmitted to a remote computing device.

Example 16 corresponds to the monitoring system of any of examples 1-3, in which, in the event of an alert, the processing block transmits a first set of data and a second set of data to the remote computing device for analysis, wherein the first set of data are generated by the 3D camera and the motion sensor prior to the alert, and wherein the second set of data are generated by the 3D camera and the motion sensor after the alert.

Example 17 corresponds to the monitoring system of any of examples 1-3, in which the monitoring system further includes stereo microphones to generate audio signals representative of sound in the vicinity of the infant, wherein the stereo microphones contain a first microphone and a second microphone, wherein the first microphone and the second microphone are positioned such that the infant lies in a line that passes through each of the first microphone and the second microphone. The processing block processes the audio signals to determine if the infant is crying.

Example 18 corresponds to the monitoring system of any of examples 1-3 and 17, further including a rocking mechanism to rock the stable surface if the processing block determines that the infant is crying.

Example 19 corresponds to the monitoring system of any of examples 1-3 and 17, in which processing block is operable to initiate one or more actions based on one or more user actions, the one or more actions including control of lights installed on the unit, changing songs played by a music system comprised in the unit, change the volume of music played by the music system, and control the operation of the rocking mechanism. The one or more user actions include a gesture of opening a hand, a gesture of hand swiping, a gesture of rotation of a hand, a gesture of placing a hand in front of the 3D camera, and a gesture of to-and-fro hand wave.

Example 20 corresponds to a monitoring system that includes a 3D (three dimensional) camera, a processing block and an alert generator. The 3D camera is used to generate images of a person. The processing block is used to process one or more of the generated images and to identify a condition with respect to the person. The alert generator is used to cause generation of an alert signal upon identification of the condition.

While various embodiments of the present invention have been described above, it should be understood that they have been presented by way of example only, and not limitation. Thus, the breadth and scope of the present invention should not be limited by any of the above-described embodiments, but should be defined only in accordance with the following claims and their equivalents.

What is claimed is:

1. A monitoring system comprising:
   a processing block to process one or more images of an infant generated by a camera, and identify a condition with respect to said infant; and
   an alert generator to cause generation of an alert signal if said identified condition warrants an external notification,
   said processing block and said alert generator are part of a unit placed in a vicinity of said infant,
   wherein said camera comprises:
      a 3D (three dimensional) camera to generate said one or more images as one or more 3D (three-dimensional) images of said infant located in a field-of-view (FoV) of said 3D camera,
   wherein said infant is placed on a surface within said FoV,
   wherein said condition is a posture of said infant, said processing block further operable to:
      extract skeletal information of said infant from said one or more 3D images;
      determine body parts of interest from said skeletal information; and
      determine said posture of said infant from said body parts of interest,
   wherein said processing block identifies said posture to be one of:
      a belly-up posture, wherein a nose and both eyes of said infant are determined to be visible, and the nose of said infant is determined to point away from said surface;
      a side posture, wherein only one ear of said infant is determined to be visible, wherein a level of a head bone of said infant is determined to be below a nearest shoulder and arm bones of said infant; and
      a belly-down posture, wherein said nose and eyes of said infant are determined not be visible, or wherein said nose is determined to be pointing towards said surface, or wherein a head of said infant is determined to be at a same level as a torso of said infant, and wherein a hip of the infant is above the torso of said infant, and wherein knees of said infant are lower than or at a same level as a rest of a leg portion of said infant,
   wherein said alert generator generates said alert signal if said processing block identifies said posture of said infant to be said belly-down posture.

2. The monitoring system of claim 1, wherein said camera is mounted on a stationary platform, wherein said surface is swingable and is within said FoV even during a motion of said surface, said monitoring system further comprising:
   a motion sensor to generate motion sensor signals representative of movements of said surface,
   wherein said one or more images contain a common motion, wherein said common motion is a sum of movements of said infant alone and movements of said surface alone,
   wherein said processing block is operable to remove from said common motion, components of motion due only to said movements of said surface alone based on said motion sensor signals received from said motion sensor.

3. The monitoring system of claim 1, wherein said extracting skeletal information, said determining body parts of interest and said determining said posture of said infant from said body parts of interest employ machine learning algorithms.

4. The monitoring system of claim 1, further comprising:
   stereo microphones to generate audio signals representative of a sound in the vicinity of said infant, wherein said stereo microphones comprise a first microphone and a second microphone, wherein said first microphone and said second microphone are positioned such that the infant lies in a line that passes through each of said first microphone and said second microphone,
   wherein said processing block is further operable to:
      filter out an ambient noise from said audio signals to generate filtered audio signals;
      determine if the eyes of said infant are open by processing a 2D (2-dimensional) image obtained by retaining only intensity components of pixels in one or more of said 3D images;
      collate data from said skeletal information, said filtered audio signals, filtered motion signals, and
      ascertain said condition from said collated data, wherein at least some operations of an ascertaining employs machine learning algorithms,
   wherein said condition is one of:
      a first state in which the eyes of said infant are determined to be open for a period of time longer than a first threshold;
      a second state in which said infant is crying;
      a third state in which movements by said infant are determined to be present for a period of time longer than a second threshold; and
      a fourth state in which said infant is determined to be in a standing or a sitting position on said surface,
   wherein said alert generator generates said alert signal upon said ascertaining.

5. The monitoring system of claim 1, wherein said processing block is further operable to:
   identify, from said posture of said infant, additional body parts exhibiting a breathing motion, wherein said additional body parts comprise the torso of said infant;
   filter out motion components in the motion of said torso that are due to a motion of said surface to generate a filtered sequence of images;
   determine moving parts in said filtered sequence, wherein said moving parts includes said torso of said infant;
   generate a grouped moving parts based on a correlating motion of adjacent parts in said moving parts; and determine a breath rate of said infant from said grouped moving parts,
wherein said alert generator generates said alert signal if said processing block determines that said breath rate falls outside of a pre-determined range.

6. The monitoring system of claim 1, wherein said processing block is further operable to:
identify, from said posture of said infant, additional body parts exhibiting a breathing motion, wherein said additional body parts comprise a face and a neck of said infant;
filter out motion components in the motion of said face and neck that are due to a motion of said surface to generate a filtered sequence of images; and
determine moving parts in said filtered sequence, wherein said moving parts includes said face and neck of said infant;
generate a grouped moving parts based on a correlating motion of adjacent parts in said moving parts;
process scene-to-scene changes in a set of 2D (2-dimensional) images to detect darkening and lightening of a skin tone of a skin of said infant, wherein said set of 2D images are obtained by retaining only intensity components of pixels in one of more of said 3D images;
filter out frequencies in said scene-to-scene changes that fall outside of a normal range of frequencies of a heart rate of an infant;
weighting and combining data representing said grouped moving parts and data representing said scene-to-scene changes; and
determining a heart rate based on an average motion of said grouped moving parts and said detection of darkening and lightening of skin tone,
wherein said alert generator generates said alert signal if said processing block determines that said heart rate falls outside a normal range.

7. The monitoring system of claim 1, wherein said condition is a presence of an insect in the vicinity of said infant.

8. The monitoring system of claim 1, wherein said processing block is further operable to:
detect, by processing said one or more 3D images, presence of a moving object between said 3D camera and said infant;
filtering out, from said one or more 3D images, objects that have a size that is outside of a normal range of sizes for insects; and
filtering out, from said one or more 3D images, moving objects that have a motion that 5 is determined not to resemble that of an insect,
wherein said alert generator generates said alert signal if said processing block detects presence of said insect.

9. The monitoring system of claim 1, wherein said alert signal is transmitted to a remote computing device.

10. The monitoring system of claim 2, wherein in an event of an alert, said processing block transmits a first set of data and a second set of data to said remote computing device for analysis,
wherein said first set of data are generated by said 3D camera and said motion sensor prior to said alert, and
wherein said second set of data are generated by said 3D camera and said motion sensor after said alert.

11. The monitoring system of claim 1, further comprising stereo microphones to generate audio signals representative of a sound in the vicinity of said infant, wherein said stereo microphones comprise a first microphone and a second microphone, wherein said first microphone and said second microphone are positioned such that said infant lies in a line that passes through each of said first microphone and said second microphone,
wherein said processing block processes said audio signals to determine if said infant is crying.

12. The monitoring system of claim 11, further comprising a rocking mechanism to rock said surface if said processing block determines that said infant is crying.

13. The monitoring system of claim 11, wherein said processing block is operable to initiate one or more actions based on one or more user actions,
wherein said one or more actions include control of lights installed on said unit, change songs played by a music system comprised in said unit, change a volume of music played by said music system, control an operation of said rocking mechanism,
wherein said one or more user actions comprise a gesture of opening a hand, a gesture of hand swiping, a gesture of rotation of a hand, a gesture of placing a hand in front of said 3D camera, and a gesture of to-and-fro hand wave.

* * * * *